United States Patent
Wada et al.

(10) Patent No.: US 9,510,805 B2
(45) Date of Patent: Dec. 6, 2016

(54) COMPLEX DIAGNOSTIC APPARATUS, COMPLEX DIAGNOSTIC SYSTEM, ULTRASOUND DIAGNOSTIC APPARATUS, X-RAY DIAGNOSTIC APPARATUS AND COMPLEX DIAGNOSTIC IMAGE-GENERATING METHOD

(71) Applicant: FUJIFILM Corporation, Tokyo (JP)

(72) Inventors: Takatsugu Wada, Ashigarakami-gun (JP); Yasunori Ohta, Ashigarakami-gun (JP); Makoto Sugizaki, Ahigarakami-gun (JP); Keiji Tsubota, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 185 days.

(21) Appl. No.: 14/487,880

(22) Filed: Sep. 16, 2014

(65) Prior Publication Data
US 2015/0087978 A1 Mar. 26, 2015

(30) Foreign Application Priority Data

Sep. 26, 2013 (JP) .................................. 2013-200121
Mar. 25, 2014 (JP) .................................. 2014-062177

(51) Int. Cl.
*A61B 8/14* (2006.01)
*A61B 8/00* (2006.01)
(Continued)

(52) U.S. Cl.
CPC ........... *A61B 8/4416* (2013.01); *A61B 6/4417* (2013.01); *A61B 6/5247* (2013.01); *A61B 6/547* (2013.01);
(Continued)

(58) Field of Classification Search
CPC ....... A61B 8/4416; A61B 8/44; A61B 6/4417; A61B 8/5261; A61B 6/5247; A61B 8/4254; A61B 8/463; A61B 6/547; A61B 6/587; A61B 8/14
(Continued)

(56) References Cited

U.S. PATENT DOCUMENTS 6,775,404 B1 * 8/2004 Pagoulatos ............... G06T 3/00
                                                             128/916
2006/0261296 A1 * 11/2006 Heath .................. A61B 6/4494
                                                             250/580
2010/0063400 A1   3/2010 Hall et al.

FOREIGN PATENT DOCUMENTS

JP          2010-57910 A      3/2010

OTHER PUBLICATIONS

Extended European Search Report, dated Feb. 12, 2015, for European Application No. 14182154.6.

* cited by examiner

*Primary Examiner* — Sanjay Cattungal
(74) *Attorney, Agent, or Firm* — Birch, Stewart, Kolasch & Birch, LLP

(57) ABSTRACT

An optimal value calculator calculates, based on angle information obtained from a first angle sensor provided in an ultrasound probe, the direction of transmission of an ultrasonic beam transmitted from the ultrasound probe, and the radiation source optimal angle of a radiation source at which the direction of radiation from the radiation source is substantially parallel to the calculated direction of transmission of the ultrasonic beam and the optimal detection angle of a radiographic image generator at which the normal of a detection surface of the radiographic image generator is substantially parallel to the calculated direction of transmission of the ultrasonic beam.

19 Claims, 8 Drawing Sheets

(51) Int. Cl.
*A61B 6/00* (2006.01)
*A61B 8/08* (2006.01)

(52) U.S. Cl.
CPC ............... *A61B 8/4254* (2013.01); *A61B 8/44* (2013.01); *A61B 8/463* (2013.01); *A61B 8/5261* (2013.01); *A61B 6/587* (2013.01); *A61B 8/14* (2013.01)

(58) Field of Classification Search
USPC .................................................. 600/437–469
See application file for complete search history.

COMPLEX DIAGNOSTIC APPARATUS, COMPLEX DIAGNOSTIC SYSTEM, ULTRASOUND DIAGNOSTIC APPARATUS, X-RAY DIAGNOSTIC APPARATUS AND COMPLEX DIAGNOSTIC IMAGE-GENERATING METHOD

CROSS-REFERENCE TO RELATED APPLICATIONS

The present application claims priority under 35 U.S.C. §119 to Japanese Patent Application No. 2013-200121, filed on Sep. 26, 2013 and Japanese Patent Application No. 2014-62177, filed on Mar. 25, 2014. Each of the above application(s) is hereby expressly incorporated by reference, in its entirety, into the present application.

BACKGROUND OF THE INVENTION

The present invention relates to a complex diagnostic apparatus, a complex diagnostic system, an ultrasound diagnostic apparatus, an X-ray diagnostic apparatus and a complex diagnostic image-generating method. The present invention more specifically relates to a complex diagnostic apparatus, a complex diagnostic system, an ultrasound diagnostic apparatus, an X-ray diagnostic apparatus and a complex diagnostic image-generating method which perform ultrasound diagnosis using ultrasound images and radiation diagnosis using radiographic images in combination.

Ultrasound diagnostic apparatuses using ultrasound images and radiation diagnostic apparatuses using radiographic images such as X-ray images have conventionally been put to practical use in the medical field.

In general, an ultrasound diagnostic apparatus includes an ultrasound probe having a built-in transducer array and an apparatus body connected to the ultrasound probe. The ultrasound probe transmits ultrasonic waves toward a subject and receives ultrasonic echoes from the subject in its respective channels, and the apparatus body electrically processes the reception signals to generate an ultrasound image.

In a radiation diagnostic apparatus, a radiation source and a radiographic image generator are disposed so as to interpose a subject therebetween. Radiation emitted from the radiation source is detected in the radiographic image generator via the subject and a radiographic image is formed in the radiographic image generator according to the detected radiation dose.

Ultrasound images and radiographic images generated by combining an ultrasound diagnostic apparatus and a radiation diagnostic apparatus with each other have recently been used in diagnosis. For example, mutually different information can be obtained from ultrasound images and radiographic images. More specifically, ultrasound images can clarify muscle, cartilage and other soft tissues in a subject's body, whereas radiographic images can clarify bone and other hard tissues. Therefore, diagnostic accuracy and efficiency can be enhanced by generating an ultrasound image and a radiographic image corresponding to the same section in a subject's body by combining an ultrasound diagnostic apparatus with a radiation diagnostic apparatus.

It is also possible to combine an ultrasound diagnostic apparatus with a radiation diagnostic apparatus so as to obtain a radiographic image including a lesion area by searching for the lesion area generated in a subject's body using an ultrasound image and irradiating the lesion area with radiation. In this process, by generating an X-ray image on a section perpendicular to a specific section in the subject's body corresponding to the ultrasound image, the X-ray image that can be obtained reliably includes the lesion area.

An ultrasound image and an X-ray image are thus required to be generated so as to accurately correspond to each other in orientation of sections in a subject's body according to the diagnosis.

A catheter which is inserted into a blood vessel or the like in a subject's body is known as a diagnostic apparatus making use of both an ultrasound image and a radiographic image. For example, JP 2010-057910 A discloses acquiring a static X-ray image and a real-time ultrasound image upon insertion of a guide wire for guiding a catheter into a subject's body and displaying the movement of the guide wire as detected by the ultrasound image on the X-ray image showing a blood vessel enhanced by contrast medium. The guide wire can be thus smoothly inserted into the blood vessel by tracking the movement of the guide wire using the ultrasound image and the X-ray image.

However, the apparatus for tracking the movement of a guide wire as described in JP 2010-057910 A uses an ultrasound image and an X-ray image to improve the efficiency of the operation for inserting the guide wire into a subject's body, and is not used to make the ultrasound image and the X-ray image accurately correspond to each other.

In order to generate an ultrasound image and an X-ray image which accurately correspond to each other in orientation of sections in a subject's body, the direction of transmission of an ultrasonic beam transmitted from an ultrasound probe is required to be substantially parallel to the direction of radiation emitted from a radiation source. However, the ultrasound probe is used as it is moved in various directions so that the diagnostic site in a subject's body can be clearly displayed, and it is difficult to accurately recognize the direction of ultrasonic beam transmission from the position of the ultrasound probe. Therefore, it is difficult to make an adjustment so that the direction of ultrasonic beam transmission may be parallel to the direction of radiation, and there is a problem that generated ultrasound images and radiographic images cannot accurately correspond to each other.

SUMMARY OF THE INVENTION

The present invention has been made to solve the above-described prior art problems and an object of the present invention is to provide a complex diagnostic apparatus and a complex diagnostic image-generating method capable of generating an ultrasound image and a radiographic image so that they may accurately correspond to each other in orientation of sections in a subject's body according to the diagnosis.

The complex diagnostic apparatus according to the present invention comprises: an ultrasound probe configured to transmit and receive an ultrasonic beam toward and from a subject; an ultrasound image generator configured to generate an ultrasound image based on reception signals outputted from the ultrasound probe; a radiation source disposed so that its placement angle is variable and configured to emit radiation toward the subject; a radiographic image generator which is disposed on a side of the subject opposite from the radiation source so that its placement angle is variable, which has a planar detection surface detecting the radiation emitted from the radiation source and which is configured to form a radiographic image according to a dose of a radiation detected on the detection surface; a first angle sensor provided in the ultrasound probe to detect a placement angle of the ultrasound probe; a second angle sensor provided in the radiation source to detect a placement angle of the radiation source; a third angle sensor provided in the radiographic image generator to detect a placement angle of the radiographic image generator; and an optimal value calculator configured to calculate, based on angle information obtained from the first angle sensor, a direction of transmission of the ultrasonic beam transmitted from the ultrasound probe, and a radiation source optimal angle of the radiation source at which a direction of radiation emitted from the radiation source is substantially parallel to the calculated direction of transmission of the ultrasonic beam and an optimal detection angle of the radiographic image generator at which a normal of the detection surface of the radiographic image generator is substantially parallel to the calculated direction of transmission of the ultrasonic beam, wherein the placement angle of the radiation source is adjusted to the radiation source optimal angle based on angle information obtained from the second angle sensor to emit the radiation and an placement angle of the detection surface of the radiographic image generator is adjusted to the optimal detection angle based on angle information obtained from the third angle sensor to detect the radiation from the radiation source.

Preferably, the ultrasound image generator generates the ultrasound image in a direction along a scanning surface of the ultrasonic beam, and the radiographic image generator generates the radiographic image in a direction orthogonal to the scanning surface of the ultrasonic beam. Preferably, the radiation source emits the radiation to an area restricted to a region of interest on the ultrasound image.

Preferably, the ultrasound image generator generates the ultrasound image in a direction orthogonal to a scanning surface of the ultrasonic beam, and the radiographic image generator generates the radiographic image in the direction orthogonal to the scanning surface of the ultrasonic beam, and wherein the ultrasound image is generated based on a plurality of ultrasound images obtained by transmission and reception of the ultrasonic beam from and in the ultrasound probe as the scanning surface is successively shifted.

The complex diagnostic apparatus can further comprise at least one of a radiation source drive controller configured to adjust the placement angle of the radiation source based on the radiation source optimal angle and a detection surface drive controller configured to adjust the placement angle of the radiographic image generator based on the optimal detection angle.

The complex diagnostic apparatus can further comprise an optimal value monitor configured to display the radiation source optimal angle and the optimal detection angle.

The complex diagnostic apparatus can further comprise position sensors provided in the ultrasound probe, the radiation source and the radiographic image generator to detect positions of the ultrasound probe, the radiation source and the radiographic image generator, respectively, wherein the radiation source and the radiographic image generator are disposed so that positional movement is possible, and wherein the optimal value calculator calculates, based on position information obtained from the position sensors, a position of transmission of the ultrasonic beam transmitted from the ultrasound probe, and a radiation source optimal position at which an irradiation axis extending in the direction of radiation emitted from the radiation source and a transmission axis extending in the direction of transmission of the ultrasonic beam overlap each other, and an optimal detection position at which the normal of the detection surface of the radiographic image generator and the transmission axis overlap each other.

The complex diagnostic apparatus can further comprise at least one of a radiation source drive controller configured to adjust a position of the radiation source based on the radiation source optimal position and a detection surface drive controller configured to adjust a position of the radiographic image generator based on the optimal detection position.

The complex diagnostic apparatus can further comprise an optimal value monitor configured to display the radiation source optimal position and the optimal detection position.

The complex diagnostic apparatus can further comprise an image monitor configured to simultaneously display the ultrasound image generated in the ultrasound image generator and the radiographic image generated in the radiographic image generator.

The image monitor can display the ultrasound image and the radiographic image on an identical scale.

The method of generating a complex diagnostic image according to the present invention comprises the steps of: performing transmission and reception of an ultrasonic beam between an ultrasound probe and a subject; generating an ultrasound image in an ultrasound image generator based on reception signals outputted from the ultrasound probe; calculating in an optimal value calculator, based on angle information obtained from a first angle sensor provided in the ultrasound probe to detect a placement angle of the ultrasound probe, a direction of transmission of the ultrasonic beam transmitted from the ultrasound probe, and a radiation source optimal angle of a radiation source at which a direction of radiation emitted from the radiation source is substantially parallel to the calculated direction of transmission of the ultrasonic beam and an optimal detection angle of a radiographic image generator at which a normal of a detection surface of the radiographic image generator is substantially parallel to the calculated direction of transmission of the ultrasonic beam; adjusting an placement angle of the radiation source to the radiation source optimal angle based on angle information obtained from a second angle sensor provided in the radiation source to emit the radiation; adjusting an placement angle of the detection surface of the radiographic image generator disposed on a side of the subject opposite from the radiation source to the optimal detection angle based on angle information obtained from a third angle sensor provided in the radiographic image generator to detect the radiation from the radiation source; and generating a radiographic image in the radiographic image generator according to a dose of a radiation detected on the detection surface.

The complex diagnostic system according to the present invention operates in combination with an ultrasound diagnostic apparatus comprising an ultrasound probe configured to transmit and receive an ultrasonic beam toward and from a subject and an ultrasound image generator configured to generate an ultrasound image based on reception signals outputted from the ultrasound probe; and a radiation diagnostic apparatus comprising a radiation source disposed so that its placement angle is variable and configured to emit radiation toward the subject, and a radiographic image generator which is disposed on a side of the subject opposite from the radiation source so that its placement angle is variable, which has a planar detection surface detecting the radiation emitted from the radiation source and which is configured to generate a radiographic image according to a dose of a radiation detected on the detection surface; the complex diagnostic system comprising: a first angle sensor for attaching to the ultrasound probe to detect a placement angle of the ultrasound probe; a second angle sensor for attaching to the radiation source to detect a placement angle of the radiation source; a third angle sensor for attaching to the radiographic image generator to detect a placement angle of the radiographic image generator; and an optimal value calculator configured to calculate, based on angle information obtained from the first angle sensor, a direction of transmission of the ultrasonic beam transmitted from the ultrasound probe, and a radiation source optimal angle of the radiation source at which a direction of radiation emitted from the radiation source is substantially parallel to the calculated direction of transmission of the ultrasonic beam and an optimal detection angle of the radiographic image generator at which a normal of the detection surface of the radiographic image generator is substantially parallel to the calculated direction of transmission of the ultrasonic beam, wherein the placement angle of the radiation source is adjusted to the radiation source optimal angle based on angle information obtained from the second angle sensor to emit the radiation and an placement angle of the detection surface of the radiographic image generator is adjusted to the optimal detection angle based on angle information obtained from the third angle sensor to detect the radiation from the radiation source.

The ultrasound diagnostic apparatus according to the present invention operates in combination with a radiation diagnostic apparatus comprising a radiation source disposed so that its placement angle is variable and configured to emit radiation toward a subject, a radiographic image generator which is disposed on a side of the subject opposite from the radiation source so that its placement angle is variable, which has a planar detection surface detecting the radiation emitted from the radiation source and which is configured to form a radiographic image according to a dose of a radiation detected on the detection surface, a first angle sensor provided in the radiation source to detect a placement angle of the radiation source, and a second angle sensor provided in the radiographic image generator to detect a placement angle of the radiographic image generator, the ultrasound diagnostic apparatus comprising: an ultrasound probe configured to transmit and receive an ultrasonic beam toward and from the subject; an ultrasound image generator configured to generate an ultrasound image based on reception signals outputted from the ultrasound probe; a third angle sensor provided in the ultrasound probe; an optimal value calculator configured to calculate, based on angle information obtained from the third angle sensor, a direction of transmission of the ultrasonic beam transmitted from the ultrasound probe to detect a placement angle of the ultrasound probe, and a radiation source optimal angle of the radiation source at which a direction of radiation emitted from the radiation source is substantially parallel to the calculated direction of transmission of the ultrasonic beam and an optimal detection angle of the radiographic image generator at which a normal of the detection surface of the radiographic image generator is substantially parallel to the calculated direction of transmission of the ultrasonic beam; and a transmitter configured to transmit the radiation source optimal angle and the optimal detection angle calculated in the optimal value calculator to the radiation diagnostic apparatus, wherein the placement angle of the radiation source is adjusted to the radiation source optimal angle based on angle information obtained from the first angle sensor to emit the radiation and an placement angle of the detection surface of the radiographic image generator is adjusted to the optimal detection angle based on angle information obtained from the second angle sensor to detect the radiation from the radiation source.

The radiation diagnostic apparatus according to the present invention operates in combination with an ultrasound diagnostic apparatus comprising an ultrasound probe configured to transmit and receive an ultrasonic beam toward and from a subject, an ultrasound image generator configured to generate an ultrasound image based on reception signals outputted from the ultrasound probe and a first angle sensor provided in the ultrasound probe to detect a placement angle of the ultrasound probe, the radiation diagnostic apparatus comprising: a radiation source disposed so that its placement angle is variable and configured to emit radiation toward the subject; a radiographic image generator which is disposed on a side of the subject opposite from the radiation source so that its placement angle is variable, which has a planar detection surface detecting the radiation emitted from the radiation source and which is configured to generate a radiographic image according to a radiation dose detected on the detection surface; a second angle sensor provided in the radiation source to detect a placement angle of the radiation source; a third angle sensor provided in the radiographic image generator to detect a placement angle of the radiographic image generator; a receiver connected to the ultrasound diagnostic apparatus to receive angle information from the first angle sensor; and an optimal value calculator configured to calculate, based on the angle information from the first angle sensor received by the receiver, a direction of transmission of the ultrasonic beam transmitted from the ultrasound probe, and a radiation source optimal angle of the radiation source at which a direction of radiation emitted from the radiation source is substantially parallel to the calculated direction of transmission of the ultrasonic beam and an optimal detection angle of the radiographic image generator at which a normal of the detection surface of the radiographic image generator is substantially parallel to the calculated direction of transmission of the ultrasonic beam; wherein the placement angle of the radiation source is adjusted to the radiation source optimal angle based on angle information obtained from the second angle sensor to emit the radiation and an placement angle of the detection surface of the radiographic image generator is adjusted to the optimal detection angle based on angle information obtained from the third angle sensor to detect the radiation from the radiation source.

According to the present invention, the radiation source optimal angle of the radiation source at which the direction of radiation emitted from the radiation source is substantially parallel to the direction of ultrasonic beam transmission and the optimal detection angle of the radiographic image generator at which the normal of the detection surface of the radiographic image generator is substantially parallel to the direction of ultrasonic beam transmission are calculated, respectively, which makes it possible to generate an ultrasound image and a radiographic image so that they may accurately correspond to each other in orientation of sections in a subject's body according to the diagnosis.

DETAILED DESCRIPTION OF THE INVENTION

Embodiment 1

Embodiment 1 of the present invention is described below based on the accompanying drawings.

Figure 1:
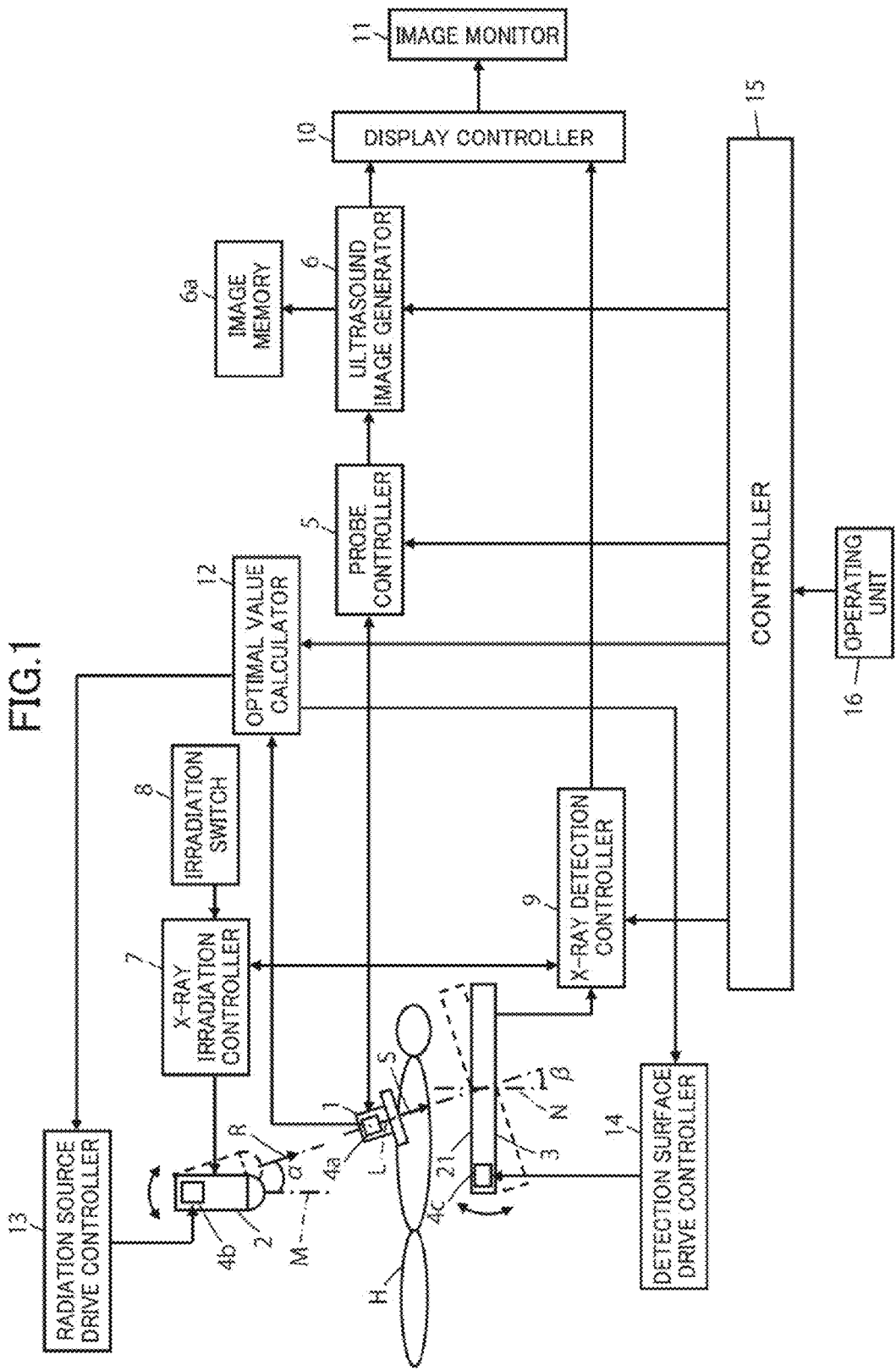
FIG. 1 is a block diagram showing the configuration of a complex diagnostic apparatus according to Embodiment 1 of the invention.

FIG. 1 shows the configuration of a complex diagnostic apparatus according to Embodiment 1 of the invention. The complex diagnostic apparatus includes an ultrasound probe 1 for transmitting ultrasonic beams in a predetermined direction toward a subject H, an X-ray source 2 for emitting X-rays toward the subject H and an X-ray image generator 3 disposed on the side of the subject opposite from the X-ray source 2. The ultrasound probe 1, the X-ray source 2 and the X-ray image generator 3 have built-in angle sensors 4a to 4c, respectively. The angle sensor 4a is provided in the ultrasound probe 1 to detect a placement angle of the ultrasound probe 1. The angle sensor 4b is provided in the X-ray source 2 to detect a placement angle of the X-ray source 2. The angle sensor 4c is provided in the X-ray image generator 3 to detect a placement angle of the X-ray image generator 3.

The ultrasound probe 1 is connected to an ultrasound image generator 6 via a probe controller 5, the X-ray source 2 to an irradiation switch 8 via an X-ray irradiation controller 7, and the X-ray image generator 3 to an X-ray detection controller 9. The ultrasound image generator 6 is connected to an image memory 6a. The ultrasound image generator 6 and the X-ray detection controller 9 are connected to a display controller 10, which in turn is connected to an image monitor 11. In addition, the X-ray irradiation controller 7 and the X-ray detection controller 9 are connected to each other.

The angle sensor 4a incorporated into the ultrasound probe 1 is connected to an optimal value calculator 12, which in turn is connected to a radiation source drive controller 13 and a detection surface drive controller 14. In addition, the radiation source drive controller 13 is connected to the angle sensor 4b incorporated into the X-ray source 2 and the detection surface drive controller 14 is connected to the angle sensor 4c incorporated into the X-ray image generator 3.

The probe controller 5, the ultrasound image generator 6, the X-ray detection controller 9 and the optimal value calculator 12 are connected to a controller 15, which in turn is connected to an operating unit 16.

Figure 2:
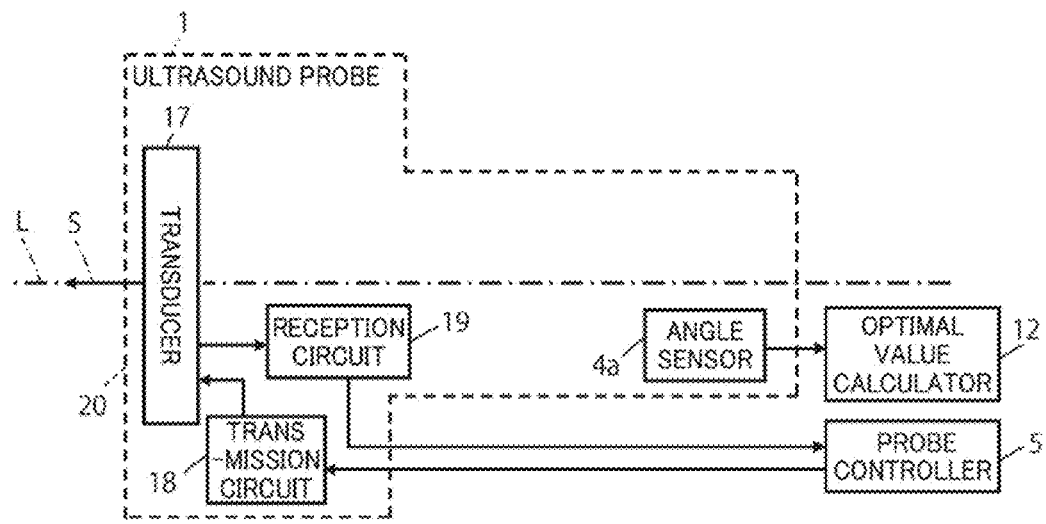
FIG. 2 is a block diagram showing the configuration of an ultrasound probe.

As shown in FIG. 2, the ultrasound probe 1 includes a one-dimensional or two-dimensional array of ultrasound transducers 17, which are connected to a transmission circuit 18 and a reception circuit 19. A transmission/reception surface 20 for use in transmission and reception of ultrasonic beams is formed at the front end of the ultrasound probe 1 in such a shape as to correspond to the array of transducers 17.

The transmission circuit 18 adjusts the delay amounts for transmission signals based on a transmission delay pattern selected by the probe controller 5 so that the ultrasonic waves transmitted from the transducers 17 via the transmission/reception surface 20 form ultrasonic beams, and supplies the transducers 17 with delay-adjusted transmission signals.

The reception circuit 19 amplifies and A/D converts the reception signals outputted from the corresponding transducers 17 to generate reception data and outputs the generated reception data to the probe controller 5.

Figure 3:
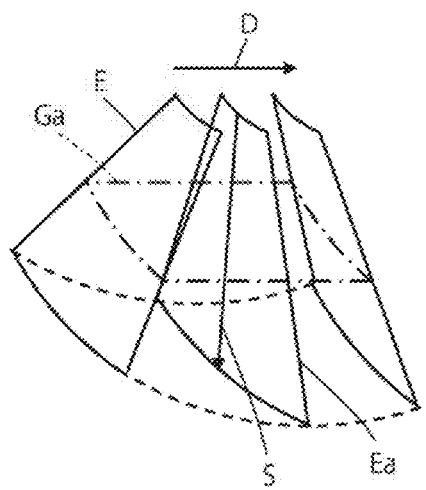
FIG. 3 is a diagram showing scanning surfaces of ultrasonic beams.

The probe controller 5 controls the respective components of the ultrasound probe 1 based on various control signals transmitted from the controller 15. More specifically, as shown in FIG. 3, the probe controller 5 controls the transmission circuit 18 and the reception circuit 19 so that scanning surfaces E of ultrasound beams are successively formed in a direction D orthogonal to the scanning surfaces E. For example, in cases where the ultrasound probe 1 having a two-dimensional array of ultrasound transducers 17 is used, the scanning surfaces E arranged in the direction D can be formed by transmitting and receiving ultrasonic beams so that the scanning surfaces E of the ultrasonic beams are successively shifted in the direction D orthogonal to the scanning surfaces E. In cases where the ultrasound probe 1 having a one-dimensional array of ultrasound transducers 17 is used, the scanning surfaces E arranged in the direction D can be formed, for example, by transmitting and receiving ultrasonic beams as the ultrasound probe 1 is successively shifted in the direction D by an operator. In this way, ultrasonic beams are successively transmitted and received along a plurality of cross-sections within a subject's body. The probe controller 5 preferably controls so that the scanning surfaces E of ultrasonic beams are parallel to each other.

The ultrasound image generator 6 generates a plurality of two-dimensional image data which are cross-sectional image information of the plurality of cross-sections within the subject's body based on the reception data generated in the reception circuit 19 of the ultrasound probe 1 and stores the generated plurality of two-dimensional image data in the image memory 6a. Ultrasound image data which is on a longitudinal section orthogonal to the cross-sections associated with the predetermined two-dimensional image data, namely which is in a direction orthogonal to the predetermined scanning surfaces E of ultrasonic beams is generated based on the plurality of two-dimensional image data stored in the image memory 6a. For example, as shown in FIG. 3, it is preferable to generate ultrasound image data Ga in a direction orthogonal to a scanning surface Ea positioned in the middle of the plurality of scanning surfaces E. The ultrasound image generator 6 outputs the generated ultrasound image data to the display controller 10 and stores it in the image memory 6a.

It should be noted that the ultrasound image generator 6 can also generate each two-dimensional image data through spatial compounding. More specifically, the ultrasound image generator 6 generates a plurality of partially overlapping image data based on reception data obtained by transmission and reception of ultrasonic beams in a plurality of directions from and to the respective ultrasound transducers 17 of the ultrasound probe 1, and converts and synthesizes the space coordinates in the plurality of image data to generate a piece of two-dimensional image data. In this way, the image quality of each two-dimensional image data and that of ultrasound image data can be improved.

On the other hand, the X-ray source 2 is disposed so that the placement angle is variable, and is provided with, for example, an X-ray tube for generating X-rays and a collimator for limiting the X-ray irradiation field to emit X-rays toward the subject. The X-ray source 2 is preferably disposed so that positional movement is possible.

The irradiation switch 8 is, for example, a two-stage push switch operated by an operator. A warm-up start signal for causing the X-ray source 2 to start warm-up is generated by pressing the switch once and an irradiation start signal for causing the X-ray source 2 to start irradiation is generated by pressing the switch twice. These signals are inputted to the X-ray irradiation controller 7.

The X-ray irradiation controller 7 is provided with a high voltage generator for supplying the X-ray source 2 with electric power. In response to input of an irradiation start signal from the irradiation switch 8, supply of electric power from the high voltage generator to the X-ray source 2 is started to cause the X-ray source 2 to emit X-rays. In response to a notice given via the X-ray detection controller 9 to inform that a sufficient dose of X-rays has reached the X-ray image generator 3, supply of electric power from the high voltage generator to the X-ray source 2 is stopped to terminate X-ray irradiation from the X-ray source 2.

The X-ray image generator 3 is disposed on the side of the subject H opposite from the X-ray source 2 so that the angle is placement variable. The X-ray image generator 3 has a planar detection surface 21 for detecting X-rays emitted from the X-ray source 2 and forms an X-ray image according to the dose of the X-rays detected on the detection surface 21.

More specifically, the X-ray image generator 3 has a DR flat panel detector. The flat panel detector includes a TFT active matrix substrate. The detection surface 21 in which a plurality of pixels for accumulating charges according to the X-ray dose reached are arrayed in a matrix is formed on the substrate. The X-rays having reached the detection surface 21 are converted into visible light by a scintillator (not shown) and the visible light obtained as a result of the conversion is subjected to photoelectric conversion in the plurality of pixels, whereby charges corresponding to the X-ray dose reached are accumulated in the respective pixels. The charges accumulated in the respective pixels are inputted to a signal processing circuit of the X-ray image generator 3 to form X-ray image data representing an X-ray image.

The X-ray image generator 3 outputs the thus formed X-ray image data to the X-ray detection controller 9. The X-ray image generator 3 is preferably disposed so that positional movement is possible.

The X-ray detection controller 9 controls the respective components of the X-ray image generator 3 based on various control signals transmitted from the controller 15. The X-ray detection generator 9 outputs the X-ray image data inputted from the X-ray image generator 3 to the display controller 10 and stores it in an image memory (not shown).

The display controller 10 causes the image monitor 11 to display an ultrasound image based on the ultrasound image data inputted from the ultrasound image generator 6. The display controller 10 also causes the image monitor 11 to display an X-ray image based on the X-ray image data inputted from the X-ray detection controller 9.

The image monitor 11 includes, for example, a display device such as an LCD, and displays the ultrasound image and the X-ray image under the control of the display controller 10.

Based on angle information obtained from at least the angle sensor 4a among the angle sensors 4a to 4c, the optimal value calculator 12 calculates the direction S of transmission of an ultrasonic beam transmitted from the ultrasound probe 1 and also calculates the radiation source optimal angle α of the X-ray source 2 at which the direction R of X-ray irradiation from the X-ray source 2 is substantially parallel to the calculated direction S of ultrasonic beam transmission and the optimal detection angle β of the X-ray image generator 3 at which the normal N of the detection surface 21 of the X-ray image generator 3 (central axis of the detection surface 21) is substantially parallel to the calculated direction S of ultrasonic beam transmission. The normal N of the detection surface 21 is preferably set on the central axis of the detection surface 21. The optimal value calculator 12 outputs the calculated radiation source optimal angle α to the radiation source drive controller 13 and the calculated optimal detection angle β to the detection surface drive controller 14.

The direction S of ultrasonic beam transmission can be set to the direction of a scanning line in any one of ultrasonic beams transmitted from the ultrasound probe 1 toward the subject H. For example, in cases where ultrasonic beams are transmitted from the two-dimensional array of ultrasound transducers 17, the direction S of ultrasonic beam transmission is preferably set, as shown in FIG. 2, on the central axis L of a housing of the ultrasound probe 1 (on the transmission axis L set along the central scanning line). In other words, the direction S of ultrasonic beam transmission is preferably set, as shown in FIG. 3, on the scanning line passing through the center of the scanning surface Ea positioned in the middle of the plurality of ultrasonic beam scanning surfaces E. In cases where two-dimensional image data corresponding to the scanning surface Ea is generated by spatial compounding, a plurality of partially overlapping scanning surfaces Ea are formed along a direction orthogonal to the direction D but the direction S of ultrasonic beam transmission can be set on the scanning line passing through the center of the scanning surface Ea positioned in the middle of the plurality of scanning surfaces Ea.

The direction R of X-ray irradiation can be set on an optical axis M of any one of X-rays emitted from the X-ray source 2 toward the subject H, and is preferably set, for example as shown in FIG. 1, on the optical axis M positioned in the center of the X-ray irradiation area.

The expression "the direction R of X-ray irradiation from the X-ray source 2 is substantially parallel to the direction S of ultrasonic beam transmission" means that the radiation source optimal angle α of the X-ray source 2 is set in an angle range of ±10° with respect to the direction S of ultrasonic beam transmission. The expression "the normal N of the detection surface 21 of the X-ray image generator 3 is substantially parallel to the direction S of ultrasonic beam transmission" means that the optimal detection angle β of the X-ray image generator 3 is set in an angle range of ±10° with respect to the direction S of ultrasonic beam transmission.

The radiation source optimal angle α is preferably set in a minimum unit range where the angle adjustment of the X-ray source 2 is possible, for example in an angle range of ±1° if the angle adjustment of the X-ray source 2 on a one-degree basis is possible, so that the direction R of X-ray irradiation from the X-ray source 2 is substantially parallel to the direction S of ultrasonic beam transmission. Likewise, the optimal detection angle β is preferably set in a minimum unit range where the angle adjustment of the X-ray image generator 3 is possible, so that the normal N of the detection surface 21 of the X-ray image generator 3 is substantially parallel to the direction S of ultrasonic beam transmission.

In cases where sections in the subject's body corresponding to an ultrasound image and an X-ray image generated in the ultrasound image generator 6 and the X-ray image generator 3, respectively, are deviated from each other at an angle equal to or larger than a predetermined value, it is preferable for the controller 15 to calculate the angle deviation between the sections corresponding to the ultrasound image and the X-ray image and for the ultrasound image generator 6 to generate again, from a plurality of two-dimensional image data, an ultrasound image of the section parallel to the section corresponding to the X-ray image based on the calculated angle deviation and angle information from the angle sensors 4a to 4c. In this way, for example, even in cases where the angles cannot be finely adjusted with respect to the direction S of ultrasonic beam transmission because the minimum unit enabling the angle adjustment of the X-ray source 2 and the X-ray image generator 3 is large, the angles can be adjusted with high accuracy by performing image processing so that the sections corresponding to the ultrasound image and the X-ray image are parallel to each other.

The radiation source drive controller 13 refers to the angle sensor 4b to adjust the placement angle of the X-ray source 2 to the radiation source optimal angle α based on the radiation source optimal angle α calculated in the optimal value calculator 12. The detection surface drive controller 14 refers to the angle sensor 4c to adjust the placement angle of the X-ray image generator 3 to the optimal detection angle β based on the optimal detection angle β calculated in the optimal value calculator 12.

The operating unit 16 is provided for an operator to perform input operations of information such as imaging conditions, and may be composed of, for example, a keyboard, a mouse, a trackball, and/or a touch panel.

The controller 15 controls the respective components in the complex diagnostic apparatus based on various instruction signals and the like inputted by the operator using the operating unit 16.

The probe controller 5, the ultrasound image generator 6, the X-ray irradiation controller 7, the X-ray detection controller 9, the display controller 10, the radiation source drive controller 13, the detection surface drive controller 14 and the controller 15 are each composed of a CPU and an operation program for causing the CPU to perform various kinds of processing; however they may be each composed of a digital circuit. In addition to a built-in hard disk, a flexible disk, an MO, an MT, a RAM, a CD-ROM, a DVD-ROM or the like may be used as the recording medium to store the operation program.

Next, the operation of Embodiment 1 is described.

First, as shown in FIG. 1, the ultrasound probe 1 is disposed on a body surface of the subject H. Transmission and reception of ultrasonic beams between the transducers 17 arrayed, for example, in a two-dimensional manner and the subject are performed as the scanning surface E is successively shifted parallel, and reception signals from the transducers 17 are inputted to the ultrasound image generator 6 via the probe controller 5.

Subsequently, the ultrasound image generator 6 generates, based on the reception signals, a plurality of two-dimensional image data corresponding to the scanning surfaces E parallel to each other, i.e., the plurality of two-dimensional image data corresponding to the cross-sections parallel to each other in the subject's body, and the plurality of two-dimensional image data are stored in the image memory 6a. Subsequently, the ultrasound image generator 6 generates an ultrasound image Ga in a direction orthogonal to the scanning surfaces E of ultrasonic beams from the plurality of two-dimensional image data stored in the image memory 6a. For example, the ultrasound image generator 6 can generate three-dimensional image data from the plurality of two-dimensional image data stored in the image memory 6a and generate the ultrasound image Ga in the direction orthogonal to the scanning surfaces E of ultrasonic beams based on the generated three-dimensional image data. Then, the thus generated ultrasound image is displayed on the image monitor 11 by the display controller 10 and is successively stored in the image memory 6a.

The operator moves the ultrasound probe 1 in various directions while checking an ultrasound image displayed on the image monitor 11, and performs a freeze operation or other operation via the operating unit 16 at a point in time when a desired ultrasound image is obtained, thereby determining an ultrasound image for use in diagnosis. In general, the operator may transmit ultrasonic beams with the ultrasound probe 1 tilted in order to obtain an ultrasound image clearly showing a diagnosis site in the subject's body, and it is difficult to determine the direction of transmission of ultrasonic beams from this position of the ultrasound probe 1. Therefore, even if X-rays are emitted from the X-ray source 2 based on the position of the ultrasound probe 1, the direction of X-ray irradiation is not parallel to the direction of ultrasonic beam transmission to generate an ultrasound image and an X-ray image different in orientation of sections in the subject's body.

Then, the optimal value calculator 12 acquires, from the angle sensor 4a provided in the ultrasound probe 1, the placement angle of the ultrasound probe 1 at which a desired ultrasound image was obtained, for example, the placement angle of the ultrasound probe 1 upon execution of the freeze operation. Subsequently, the optimal value calculator 12 calculates, based on the angle information acquired from the angle sensor 4a, the direction S of ultrasonic beam transmission at a point in time when the desired ultrasound image was obtained.

Here, the direction S of ultrasonic beam transmission is deemed to be set on the central axis L of the ultrasound probe 1, as shown in FIG. 2.

The optimal value calculator 12 calculates the radiation source optimal angle α of the X-ray source 2 at which the direction R of X-ray irradiation from the X-ray source 2 is substantially parallel to the direction S of ultrasonic beam transmission and also calculates the optimal detection angle β of the X-ray image generator 3 at which the normal N of the detection surface 21 of the X-ray image generator 3 is substantially parallel to the direction S of ultrasonic beam transmission.

The optimal value calculator 12 outputs the calculated radiation source optimal angle α to the radiation source drive controller 13 and the calculated optimal detection angle β to the detection surface drive controller 14.

The radiation source drive controller 13 adjusts the placement angle of the X-ray source 2 to the radiation source optimal angle α while referring to the angle sensor 4b provided in the X-ray source 2, and the detection surface drive controller 14 adjusts the placement angle of the X-ray image generator 3 to the optimal detection angle β while referring to the angle sensor 4c provided in the X-ray image generator 3.

In this way, the direction R of X-ray irradiation from the X-ray source 2 is made substantially parallel to the direction S of ultrasonic beam transmission and, with respect to the previously obtained ultrasound image in a direction orthogonal to the scanning surfaces E of ultrasonic beams, an X-ray image in a direction which is likewise orthogonal to the scanning surfaces E of ultrasonic beams can be generated, and the ultrasound image and the X-ray image that can be generated correspond to the sections parallel to each other in the subject's body. In addition, the normal N of the detection surface 21 of the X-ray image generator 3 is made substantially parallel to the direction R of X-ray irradiation, and the X-ray image generator 3 can receive X-rays from the X-ray source 2 in a direction orthogonal to the detection surface 21 and reliably reflect the X-rays having reached the detection surface 21 on the X-ray image.

The radiation source drive controller 13 preferably moves the position of the X-ray source 2 based on the transmission position of the ultrasound probe 1 so that an irradiation axis M extending in the direction R of irradiation from the X-ray source and the transmission axis L extending in the direction S of ultrasonic beam transmission overlap each other. In this way, the paths of ultrasonic beams and X-rays in the subject's body can be made to coincide with each other to generate an ultrasound image and an X-ray image which are parallel to each other in the subject's body and correspond to a section at the same position.

The detection surface drive controller 14 preferably moves the position of the X-ray image generator 3 based on the transmission position of the ultrasound probe 1 so that the normal N of the detection surface 21 in the X-ray image generator 3 and the transmission axis L extending in the direction S of ultrasonic beam transmission overlap each other. In this way, X-rays having passed through the subject's body can be detected in the central portion of the detection surface 21 and the X-rays having reached the detection surface 21 can be reliably reflected on the X-ray image.

Subsequently, upon pressing the irradiation switch 8, electric power suitable to the imaging conditions is supplied from the X-ray irradiation controller 7 to the X-ray source 2 after the end of warm-up of the X-ray source 2 and X-rays are emitted in the direction R of irradiation from the X-ray source 2 whose angle is adjusted to the radiation source optimal angle α.

The X-rays emitted from the X-ray source 2 pass through the subject's body along the same path as ultrasonic beams, and are made to be incident on the detection surface 21 of the X-ray image generator 3 whose angle is adjusted to the optimal detection angle β in a direction perpendicular to the detection surface 21. When the X-rays having passed through the subject's body are thus detected in the X-ray image generator 3, the X-ray image generator 3 accumulates signal charges according to the detected X-ray dose to form an X-ray image.

The X-ray image formed in the X-ray image generator 3 is outputted to the display controller 10 via the X-ray detection controller 9 and is displayed on the image monitor 11 by the display controller 10.

In the thus obtained X-ray image, position deviation or the like in the previously obtained ultrasound image is suppressed, which enables a detailed comparison between the ultrasound image superior in clarifying a soft tissue in the subject's body and the X-ray image superior in clarifying a hard tissue in the subject's body.

For example, by imaging a peripheral portion of the heart in the subject's body and comparing an ultrasound image clearly showing the heart and blood vessels and an X-ray image clearly showing the ribs and the like present on the periphery of the heart, a complex phenomenon as in a case where a heart disorder is caused by vascular compression due to bone fracture can be examined in detail.

Symptoms such as muscle strain and bone fracture that are observable on only one of an ultrasound image and an X-ray image can be observed at a time and the cause of the symptoms can be accurately determined.

Figure 4:
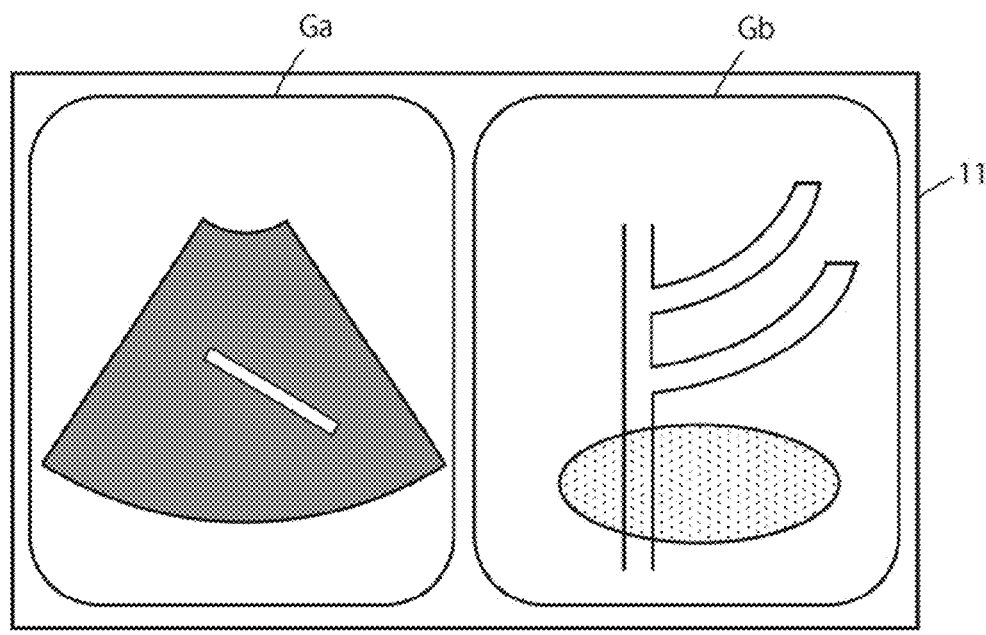
FIG. 4 is a diagram showing how images are displayed on an image monitor.

As shown in FIG. 4, the display controller 10 preferably causes the image monitor 11 to simultaneously display an ultrasound image Ga generated in the ultrasound image generator 6 and an X-ray image Gb generated in the X-ray image generator 3 side by side. A more detailed diagnosis can be made by thus displaying the ultrasound image Ga and the X-ray image Gb simultaneously.

Furthermore, the display controller 10 preferably causes the image monitor 11 to display the ultrasound image Ga and the X-ray image Gb on the same scale. The ultrasound image Ga can be thereby more accurately compared with the X-ray image Gb, thus enabling a more detailed diagnosis.

According to the embodiment under consideration, by making the direction of X-ray irradiation substantially parallel to the direction S of ultrasonic beam transmission and also making the normal of the detection surface of the X-ray image generator 3 substantially parallel to the direction S of ultrasonic beam transmission, an ultrasound image and an X-ray image corresponding to sections which are parallel to each other in the subject's body can be generated. Occurrence of directional deviation in the sections in the subject's body corresponding to the ultrasound image and the X-ray image is thereby suppressed and hence the diagnosis accuracy can be enhanced by comparing in detail the ultrasound image and the X-ray image having information different from each other.

Embodiment 2

According to Embodiment 1, the sections in the subject's body corresponding to an ultrasound image and an X-ray image were positioned so as to be oriented parallel to each other by making the direction of X-ray irradiation substantially parallel to the direction of ultrasonic beam transmission and also making the normal of the detection surface of the X-ray image generator substantially parallel to the direction of ultrasonic beam transmission. However, positioning is not limited to this as long as an ultrasound image and an X-ray image can be generated so as to accurately correspond to each other in orientation of sections in the subject's body according to the diagnosis. For example, the sections in the subject's body corresponding to the ultrasound image and the X-ray image may also be positioned so as to be oriented orthogonal to each other.

Figure 5:
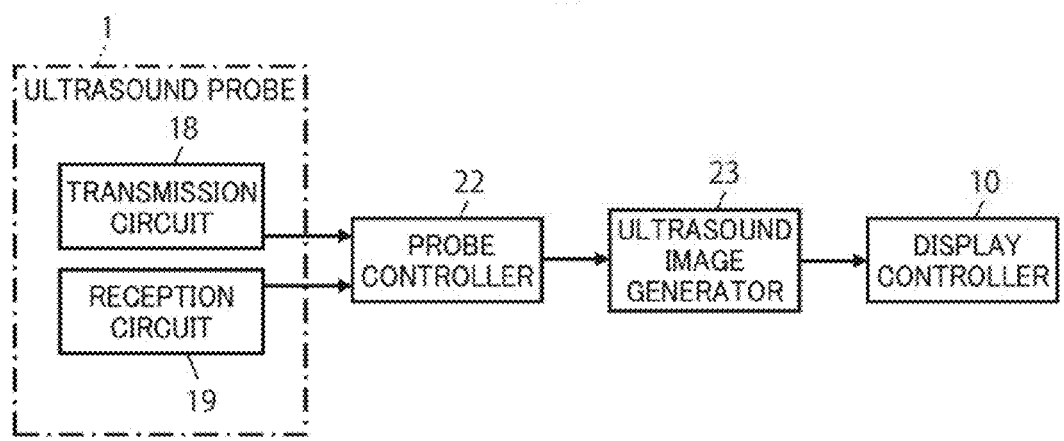
FIG. 5 is a block diagram showing the configuration of an essential part of a complex diagnostic apparatus according to Embodiment 2 of the invention.

For example in the complex diagnostic apparatus according to Embodiment 1, the probe controller 5 may be replaced by a probe controller 22 and the ultrasound image generator 6 by an ultrasound image generator 23, as shown in FIG. 5.

The probe controller 22 controls a transmission circuit 18 and a reception circuit 19 so as to perform transmission and reception of ultrasonic waves to and from the subject's body.

The ultrasound image generator 23 generates two-dimensional image data which is sectional image information of cross-sections in the subject's body, namely, ultrasound image data in a direction along the ultrasonic beam scanning surface E based on reception data generated in the reception circuit 19 of the ultrasound probe 1. The ultrasound image generator 23 outputs the generated ultrasound image data to the display controller 10 and stores it in the image memory 6a.

Next, the operation of Embodiment 2 is described.

Transmission and reception of ultrasonic beams between the transducers 17 of the ultrasound probe 1 disposed on a body surface of the subject H and the subject's body are performed, and the ultrasound image generator 23 generates an ultrasound image in the direction along the ultrasonic beam scanning surface E based on reception signals from the transducers 17.

An operator moves the ultrasound probe 1 in various directions while checking an ultrasound image displayed on the image monitor 11, and performs a freeze operation or other operation via the operating unit 16 at a point in time when a desired ultrasound image is obtained, thereby determining an ultrasound image for use in diagnosis. For example, the operator can determine an image in which a lesion area was found, as an ultrasound image for use in diagnosis.

Subsequently, as in Embodiment 1, the optimal value calculator 12 acquires, from the angle sensor 4a provided in the ultrasound probe 1, the placement angle of the ultrasound probe 1 at which the desired ultrasound image was obtained, and calculates the direction S of ultrasonic beam transmission at a point in time when the desired ultrasound image was obtained.

The direction S of ultrasonic beam transmission can be set to the direction of a scanning line in any one of ultrasonic beams transmitted from the ultrasound probe 1 toward the subject H, and is preferably set on the central axis L of the housing of the ultrasound probe 1 (on the transmission axis L set along the central scanning line), for example as shown in FIG. 2. In cases where two-dimensional image data is generated by spatial compounding, a plurality of partially overlapping scanning surfaces are formed but the direction S of ultrasonic beam transmission can be set on the scanning line passing through the center of the scanning surface positioned in the middle of the plurality of scanning surfaces.

The optimal value calculator 12 calculates the radiation source optimal angle α of the X-ray source 2 at which the direction R of X-ray irradiation from the X-ray source 2 is substantially parallel to the direction S of ultrasonic beam transmission and also calculates the optimal detection angle β of the X-ray image generator 3 at which the normal N of the detection surface 21 of the X-ray image generator 3 is substantially parallel to the direction S of ultrasonic beam transmission.

The calculated radiation source optimal angle α is inputted to the radiation source drive controller 13. The radiation source drive controller 13 adjusts the placement angle of the X-ray source 2 to the radiation source optimal angle α. The optimal detection angle β is inputted to the detection surface drive controller 14. The detection surface drive controller 14 adjusts the placement angle of the X-ray image generator 3 to the optimal detection angle β.

The direction R of X-ray irradiation from the X-ray source 2 is thereby made substantially parallel to the direction S of ultrasonic beam transmission to generate an X-ray image in a direction orthogonal to the ultrasonic beam scanning surfaces E and the sections in the subject's body corresponding to the ultrasound image and the X-ray image can be positioned so as to be oriented orthogonal to each other. In addition, the normal N of the detection surface 21 of the X-ray image generator 3 is made substantially parallel to the direction R of X-ray irradiation, and the X-ray image generator 3 can receive X-rays from the X-ray source 2 in a direction orthogonal to the detection surface 21 and reliably reflect the X-rays having reached the detection surface 21 on the X-ray image.

According to the embodiment under consideration, the sections in the subject's body corresponding to the ultrasound image and the X-ray image can be positioned so as to be oriented orthogonal to each other by making the direction of X-ray irradiation substantially parallel to the direction S of ultrasonic beam transmission and also making the normal of the detection surface of the X-ray image generator substantially parallel to the direction S of ultrasonic beam transmission. The X-ray image that can be thus generated reliably contains the lesion area taken on the ultrasound image and the dose of radiation to which the subject's body is exposed can be prevented from increasing due to X-ray irradiation toward a direction where there is no lesion area.

The complex diagnostic apparatus according to the embodiment under consideration can be advantageously used in subjects in whom the X-ray irradiation is desirably reduced to the minimum possible level, as exemplified by pregnant women, newborns and infants.

In addition, according to the embodiment under consideration, an X-ray image is generated so as to reliably include a lesion area after the lesion area has been checked on an ultrasound image and hence the number of times the subject's body is exposed to X-rays can be suppressed as compared with a case where only an X-ray image is generated to search for the lesion area. Therefore, effects of X-rays on people living on the periphery of an examination area in clinical examinations performed, for example, in a disaster site and a temporary dispensary can be suppressed. In cases where a portable X-ray apparatus is used to generate X-ray images, its battery can also be saved.

In addition, according to the embodiment under consideration, an ultrasound image is used to obtain information on the cross-section of a subject's body and an X-ray image is used to obtain information on the longitudinal section of the subject's body, and hence a complex diagnosis using the ultrasound image and the X-ray image is made possible without generating a three-dimensional image using, for example, computed tomography (CT) and magnetic resonance imaging (MR). Therefore, the complex diagnostic apparatus can be advantageously used in cases where low cost is required in clinical examinations as in animal hospitals and small-sized clinics.

Furthermore, according to the embodiment under consideration, the placement angle of the X-ray source is adjusted based on angle information of the ultrasound probe 1 so that a lesion area is adequately exposed to X-rays, and hence even in cases where it is difficult to perform positioning of the direction of X-ray irradiation with respect to patients including, for example, patients to be radiographed in an oblique position and ICU patients, the lesion area can be adequately exposed to X-rays. In this process, a reference angle sensor which serves as a reference of the angle sensors 4a to 4c is preferably attached to the subject's body. The orientations of the ultrasound probe 1, the X-ray source 2 and the detection surface 21 can be adjusted with high accuracy based on angle information of the subject's body obtained from the reference angle sensor.

The X-ray source 2 preferably emits X-rays toward an area restricted to a region of interest on an ultrasound image. For example, an operator sets a region of interest in a lesion area found on an ultrasound image. The controller 15 outputs information on the set region of interest to the X-ray irradiation controller 7 and the X-ray detection controller 9. Subsequently, the X-ray irradiation controller 7 controls the X-ray source 2 so that X-rays are emitted to an area restricted to the region of interest, and the X-rays having passed through the lesion area in the subject's body are detected on the detection surface 21 of the X-ray image generator 3 controlled by the X-ray detection controller 9.

The exposure dose of the subject's body can be thus further reduced by restricting X-ray irradiation to the lesion area in the subject's body.

Figure 6:
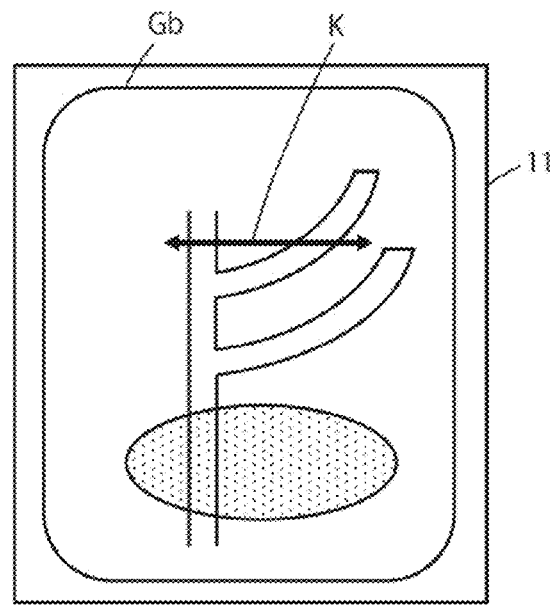
FIG. 6 is a diagram showing how a marker is displayed on an X-ray image at a position corresponding to an ultrasound image.

As shown in FIG. 6, the controller 15 preferably displays a marker K showing a cross-section in the subject's body corresponding to the previously obtained ultrasound image on an X-ray image Gb displayed on the image monitor 11 based on angle information of the ultrasound probe 1 obtained from the optimal value calculator 12. The position of the lesion area found on the ultrasound image can be thereby easily seen to make a detailed diagnosis using the X-ray image. Information on the X-ray image and the marker K is preferably stored in, for example, a console (not shown) as complex information so as to be utilized in the subsequent diagnosis.

Embodiment 3

Figure 7:
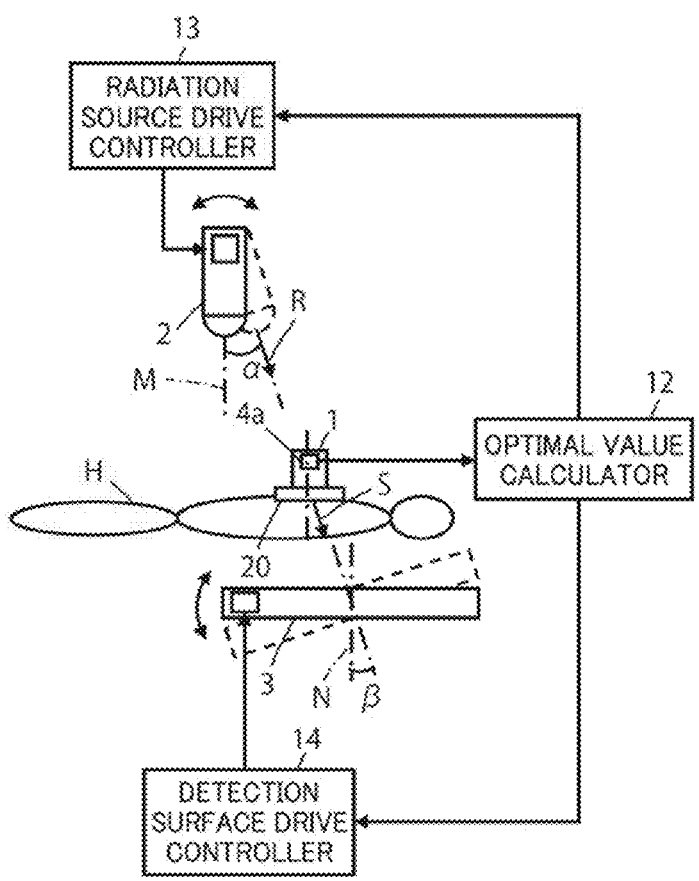
FIG. 7 is a block diagram showing the configuration of an essential part of a complex diagnostic apparatus according to Embodiment 3 of the invention.

According to Embodiments 1 and 2 as described above, the optimal value calculator 12 sets the direction S of ultrasonic beam transmission on the central axis of the ultrasound probe 1. However, for example in cases where an ultrasonic beam is to be transmitted is steered in an oblique direction with respect to the transmission/reception surface 20 of the ultrasound probe 1 as shown in FIG. 7, the direction of transmission of the steered ultrasonic beam is preferably set as the direction S of ultrasonic beam transmission.

The optimal value calculator 12 calculates the direction S of transmission of the steered ultrasonic beam based on angle information from the angle sensor 4a provided in the ultrasound probe 1 and the direction of steering of the ultrasonic beam set in the controller 15. Subsequently, the optimal value calculator 12 calculates the radiation source optimal angle α of the X-ray source 2 at which the direction R of X-ray irradiation from the X-ray source 2 is substantially parallel to the direction S of transmission of the steered ultrasonic beam and also calculates the optimal detection angle β of the X-ray image generator 3 at which the normal N of the detection surface 21 of the X-ray image generator 3 is substantially parallel to the direction S of transmission of the steered ultrasonic beam. The radiation source drive controller 13 adjusts the placement angle of the X-ray source 2 to the radiation source optimal angle α, and the detection surface drive controller 14 adjusts the placement angle of the X-ray image generator 3 to the optimal detection angle β.

In this way, the direction S of transmission of the steered ultrasonic beam, the direction R of X-ray irradiation from the X-ray source 2, and the normal N of the detection surface 21 of the X-ray image generator 3 can be made substantially parallel to each other, whereby an ultrasound image and an X-ray image can be generated so as to accurately correspond to each other in orientation of sections in the subject's body according to the diagnosis.

Embodiment 4

According to Embodiments 1 to 3 as described above, the radiation source drive controller 13 and the detection surface drive controller 14 are used to adjust the placement angles of the X-ray source 2 and the X-ray image generator 3. However, the complex diagnostic apparatus may also be configured to include one of the radiation source drive controller 13 and the detection surface drive controller 14.

The complex diagnostic apparatus preferably includes an optimal value monitor which displays the radiation source optimal angle α and the optimal detection angle β calculated in the optimal value calculator 12.

For example, if the detection surface drive controller 14 is excluded while providing the optimal value monitor for displaying the optimal detection angle β, an operator can adjust the placement angle of the X-ray image generator 3 by checking the optimal detection angle β on the optimal value monitor.

Embodiment 5

Figure 8:
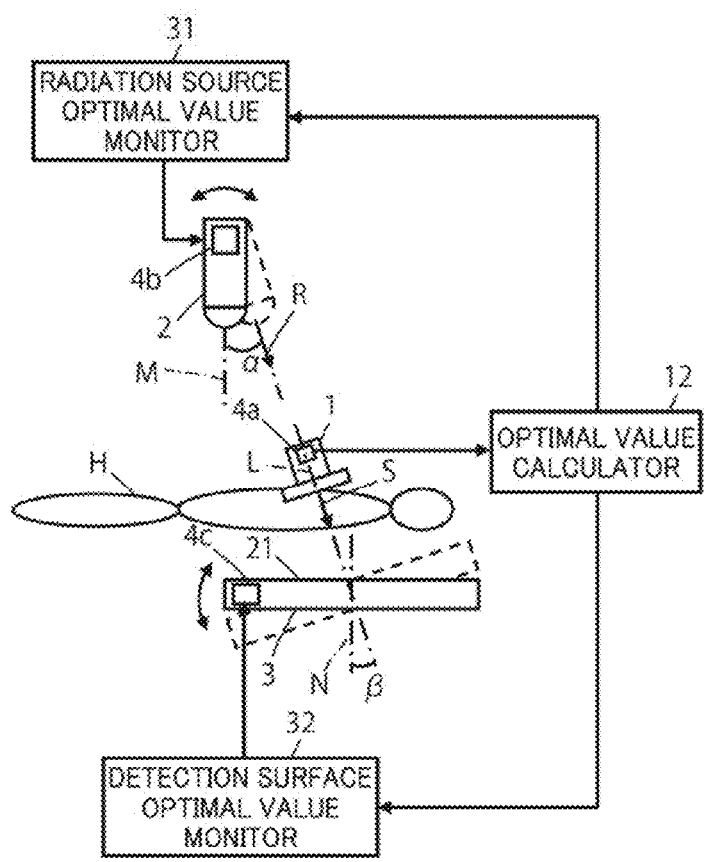
FIG. 8 is a block diagram showing the configuration of an essential part of a complex diagnostic apparatus according to Embodiment 5 of the invention.

An essential part of the configuration of a complex diagnostic apparatus according to Embodiment 5 is shown in FIG. 8. This complex diagnostic apparatus is obtained by replacing the radiation source drive controller 13 in the complex diagnostic apparatuses according to Embodiments 1 to 4 with a radiation source optimal value monitor 31 and the detection surface drive controller 14 with a detection surface optimal value monitor 32. The radiation source optimal value monitor 31 and the detection surface optimal value monitor 32 constitute the optimal value monitors in the present invention.

The optimal value calculator 12 calculates the direction S of ultrasonic beam transmission based on angle information from the angle sensor 4a provided in the ultrasound probe 1 and also calculates the radiation source optimal angle α of the X-ray source 2 and the optimal detection angle β of the X-ray image generator 3. The optimal value calculator 12 outputs the radiation source optimal angle α to the radiation source optimal value monitor 31 and the optimal detection angle β to the detection surface optimal value monitor 32. Angle information from the angle sensor 4b provided in the X-ray source 2 is inputted to the radiation source optimal value monitor 31, whereas angle information from the angle sensor 4c provided in the X-ray image generator 3 is inputted to the detection surface optimal value monitor 32.

The radiation source optimal angle α and the placement angle of the X-ray source 2 are thus displayed on the radiation source optimal value monitor 31 so that the operator can adjust the placement angle of the X-ray source 2 to the radiation source optimal angle α based on the display. Likewise, the optimal detection angle β and the placement angle of the X-ray image generator 3 are displayed on the detection surface optimal value monitor 32 so that the operator can adjust the placement angle of the X-ray image generator 3 to the optimal detection angle β based on the display.

The complex diagnostic apparatus can be downsized by excluding the radiation source drive controller 13 and the detection surface drive controller 14 in this way and, for example, a transportable complex diagnostic apparatus in which the placement angles and the positions of the X-ray source 2 and the X-ray image generator 3 are changeable freehand can be provided.

According to the embodiment under consideration, in the case of the transportable complex diagnostic apparatus, the exclusion of the radiation source drive controller 13 and the detection surface drive controller 14 as described above makes it difficult to have the direction S of ultrasonic beam transmission and the direction R of X-ray irradiation coincide with each other but these directions may easily coincide with each other by providing the optimal value monitors, whereby an ultrasound image and an X-ray image can be generated so as to accurately correspond to each other in orientation of sections in the subject's body according to the diagnosis.

Embodiment 6

Figure 9:
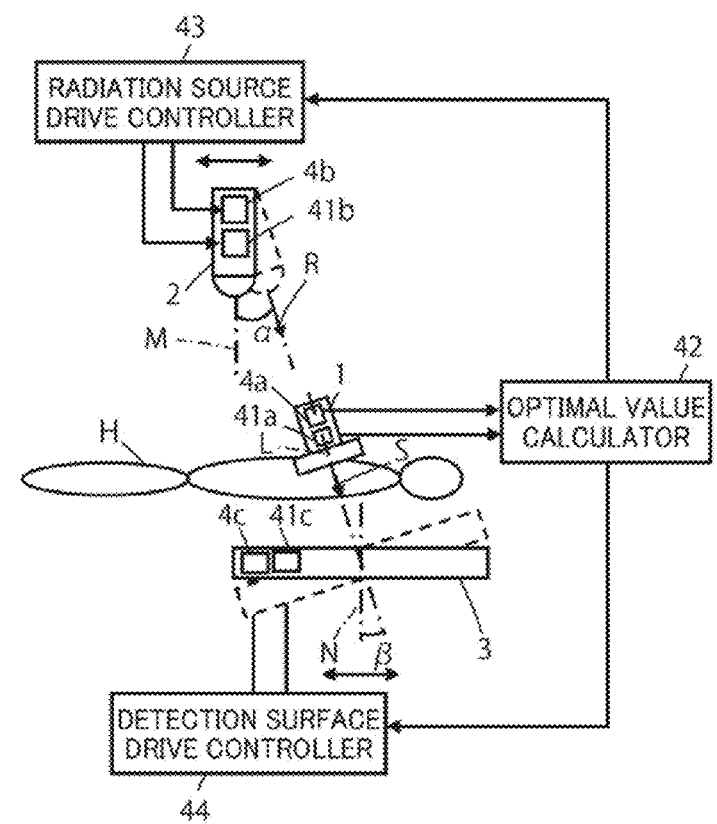
FIG. 9 is a block diagram showing the configuration of an essential part of a complex diagnostic apparatus according to Embodiment 6 of the invention.

An essential part of the configuration of a complex diagnostic apparatus according to Embodiment 6 is shown in FIG. 9. This complex diagnostic apparatus is obtained by newly providing the ultrasound probe 1, the X-ray source 2 and the X-ray image generator 3 in the complex diagnostic apparatuses in Embodiments 1 to 4 with position sensors 41a to 41c, respectively, and connecting the position sensors 41a to 41c to an optimal value calculator 42, a radiation source drive controller 43 and a detection surface drive controller 44, respectively. The X-ray source 2 and the X-ray image generator 3 are assumed to be disposed so that the placement angles and the positions are variable.

The position sensors 41a to 41c are provided in the ultrasound probe 1, the X-ray source 2 and the X-ray image generator 3 to detect positions of the ultrasound probe 1, the X-ray source 2 and the X-ray image generator 3, respectively.

Based on position information from the position sensor 41a provided in the ultrasound probe 1, the optimal value calculator 42 calculates the position of transmission of an ultrasonic beam transmitted from the ultrasound probe 1 and also calculates the radiation source optimal position at which the irradiation axis M extending in the direction R of irradiation from the X-ray source 2 and the transmission axis L extending in the direction of ultrasonic beam transmission overlap each other, and the optimal detection position at which the normal N of the detection surface 21 of the X-ray image generator 3 and the transmission axis L overlap each other. Subsequently, the optimal value calculator 42 outputs the calculated radiation source optimal position to the radiation source drive controller 43 and the calculated optimal detection position to the detection surface drive controller 44.

The radiation source drive controller 43 adjusts the placement angle of the X-ray source 2 to the radiation source optimal angle α and the position of the X-ray source 2 to the radiation source optimal position while referring to the angle sensor 4b and the position sensor 41b provided in the X-ray source 2. The detection surface drive controller 44 adjusts the placement angle of the X-ray image generator 3 to the optimal detection angle β and the position of the X-ray image generator 3 to the optimal detection position while referring to the angle sensor 4c and the position sensor 41c provided in the X-ray image generator 3.

According to the embodiment under consideration, it is possible to make the irradiation axis M of X-rays and the normal N of the detection surface 21 of the X-ray image generator 3 exactly coincident with the transmission axis L of an ultrasonic beam, whereby an ultrasound image and an X-ray image can be generated so as to accurately correspond to each other in orientation of sections in the subject's body according to the diagnosis.

The complex diagnostic apparatus may also be configured to include one of the radiation source drive controller 43 and the detection surface drive controller 44.

In cases where sections in the subject's body corresponding to an ultrasound image and an X-ray image generated in the ultrasound image generator 6 and the X-ray image generator 3, respectively, are deviated in position from each other at a distance equal to or larger than a predetermined value, it is preferable for the controller 15 to calculate the position deviation between the sections corresponding to the ultrasound image and the X-ray image and for the ultrasound image generator 6 to generate again, from a plurality of two-dimensional image data, an ultrasound image of the section coincident in position with the section corresponding to the X-ray image based on the calculated position deviation and position information from the position sensors 41a to 41c.

Embodiment 7

Figure 10:
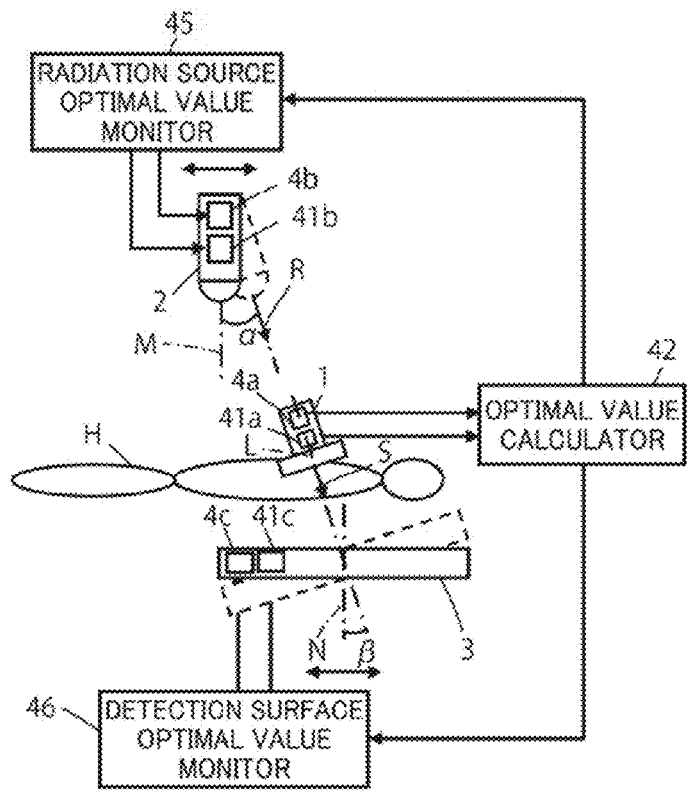
FIG. 10 is a block diagram showing the configuration of an essential part of a complex diagnostic apparatus according to Embodiment 7 of the invention.

An essential part of the configuration of a complex diagnostic apparatus according to Embodiment 7 is shown in FIG. 10. This complex diagnostic apparatus is obtained by replacing the radiation source drive controller 43 in the complex diagnostic apparatus according to Embodiment 6 with a radiation source optimal value monitor 45 and the detection surface drive controller 44 with a detection surface optimal value monitor 46. The radiation source optimal value monitor 45 and the detection surface optimal value monitor 46 constitute the optimal value monitors in the present invention.

The radiation source optimal value monitor 45 displays the radiation source optimal angle α and the radiation source optimal position outputted from the optimal value calculator 42 and also displays angle information and position information respectively derived from the angle sensor 4b and the position sensor 41b provided in the X-ray source 2. The detection surface optimal value monitor 46 displays the optimal detection angle β and the optimal detection position outputted from the optimal value calculator 42 and also displays angle information and position information respectively derived from the angle sensor 4c and the position sensor 41c provided in the X-ray image generator 3.

An operator thereby adjusts the placement angle and the position of the X-ray source 2 and the placement angle and the position of the X-ray image generator 3 based on the display on the radiation source optimal value monitor 45 and the detection surface optimal value monitor 46.

According to the embodiment under consideration, as in the above-described Embodiment 5, the complex diagnostic apparatus can be downsized by excluding the radiation source drive controller 43 and the detection surface drive controller 44 and, for example, a transportable complex diagnostic apparatus in which the placement angles and the positions of the X-ray source 2 and the X-ray image generator 3 are changeable freehand can be provided.

Embodiment 8

Embodiments 1 to 7 are configured from the complex diagnostic apparatuses each including the ultrasound probe 1, the ultrasound image generator 6, the X-ray source 2 and the X-ray image generator 3. However, the present invention may also be configured from a complex diagnostic system which operates in combination with an ultrasound diagnostic apparatus including an ultrasound probe 1 and an ultrasound image generator 6 with an X-ray diagnostic apparatus including an X-ray source 2 and an X-ray image generator 3.

In other words, the complex diagnostic system includes angle sensors for attaching to an ultrasound probe, an X-ray source and an X-ray image generator, respectively, and an optimal value calculator for calculating, based on angle information obtained from the angle sensors, the direction of transmission of an ultrasonic beam transmitted from the ultrasound probe, and the radiation source optimal angle of the X-ray source at which the direction of X-ray irradiation from the X-ray source is substantially parallel to the calculated direction of ultrasonic beam transmission and the optimal detection angle of the X-ray image generator at which the normal of a detection surface of the X-ray image generator is substantially parallel to the calculated direction of ultrasonic beam transmission.

Figure 11:
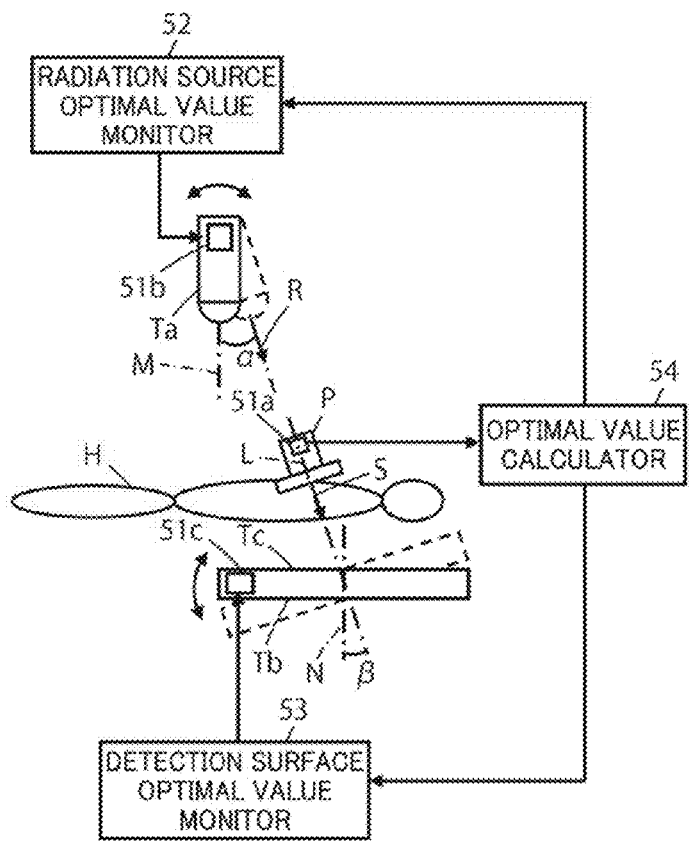
FIG. 11 is a block diagram showing the configuration of a complex diagnostic system according to Embodiment 8 of the invention.

For example, the complex diagnostic system includes, as shown in FIG. 11, angle sensors 51a to 51c, a radiation source optimal value monitor 52 connected to the angle sensor 51b, a detection surface optimal value monitor 53 connected to the angle sensor 51c, and an optimal value calculator 54 connected to the angle sensor 51a, the radiation source optimal value monitor 52 and the detection surface optimal value monitor 53.

When combining an ultrasound diagnostic apparatus and an X-ray diagnostic apparatus using the complex diagnostic system, the angle sensor 51a is attached to an ultrasound probe P provided in the ultrasound diagnostic apparatus and the angle sensors 51b and 51c are attached to an X-ray source Ta and an X-ray image generator Tb provided in the X-ray diagnostic apparatus.

Based on angle information obtained from the angle sensor 51a, the optimal value calculator 54 calculates the direction S of transmission of an ultrasonic beam transmitted from the ultrasound probe P and also calculates the radiation source optimal angle α of the X-ray source Ta at which the direction R of X-ray irradiation from the X-ray source Ta is substantially parallel to the calculated direction S of ultrasonic beam transmission and the optimal detection angle β of the X-ray image generator Tb at which the normal of a detection surface Tc of the X-ray image generator Tb is substantially parallel to the calculated direction S of ultrasonic beam transmission.

The radiation source optimal angle α and the placement angle of the X-ray source Ta are displayed on the radiation source optimal value monitor 52 so that an operator adjusts the placement angle of the X-ray source Ta to the radiation source optimal angle α based on the display. The optimal detection angle β and the placement angle of the X-ray image generator Tb are likewise displayed on the detection surface optimal value monitor 53 so that the operator adjusts the placement angle of the X-ray image generator Tb to the optimal detection angle β based on the display.

By thus combining an ultrasound diagnostic apparatus and an X-ray diagnostic apparatus using the complex diagnostic system, diagnosis can be carried out in the same manner as with the complex diagnostic apparatus according to Embodiment 5.

According to the embodiment under consideration, an ultrasound image and an X-ray image can be generated so as to accurately correspond to each other in orientation of sections in the subject's body according to the diagnosis. Particularly in cases where a transportable ultrasound diagnostic apparatus is combined with a transportable X-ray diagnostic apparatus, it is difficult to make the direction S of ultrasonic beam transmission coincident with the direction R of X-ray irradiation but these directions can be easily made coincident with each other by using the complex diagnostic system of the present invention.

Embodiment 9

Embodiments 1 to 7 are configured from the complex diagnostic apparatuses each including the ultrasound probe 1, the ultrasound image generator 6, the X-ray source 2 and the X-ray image generator 3 in an integrated form. However, the present invention may also be configured from an ultrasound diagnostic apparatus which operates in combination with an X-ray diagnostic apparatus including an X-ray source, an X-ray image generator, a first angle sensor provided in the X-ray source and a second angle sensor provided in the X-ray image generator.

In other words, the ultrasound diagnostic apparatus according to the embodiment under consideration includes an ultrasound probe, an ultrasound image generator, a third angle sensor provided in the ultrasound probe, an optimal value calculator for calculating, based on angle information obtained from the third angle sensor, the direction of transmission of an ultrasonic beam transmitted from the ultrasound probe, and the radiation source optimal angle of the X-ray source at which the direction of X-ray irradiation from the X-ray source is substantially parallel to the calculated direction of ultrasonic beam transmission and the optimal detection angle of the X-ray image generator at which the normal of a detection surface of the X-ray image generator is substantially parallel to the calculated direction of ultrasonic beam transmission, and a transmitter for transmitting the radiation source optimal angle and the optimal detection angle calculated in the optimal value calculator to the X-ray diagnostic apparatus.

Figure 12:
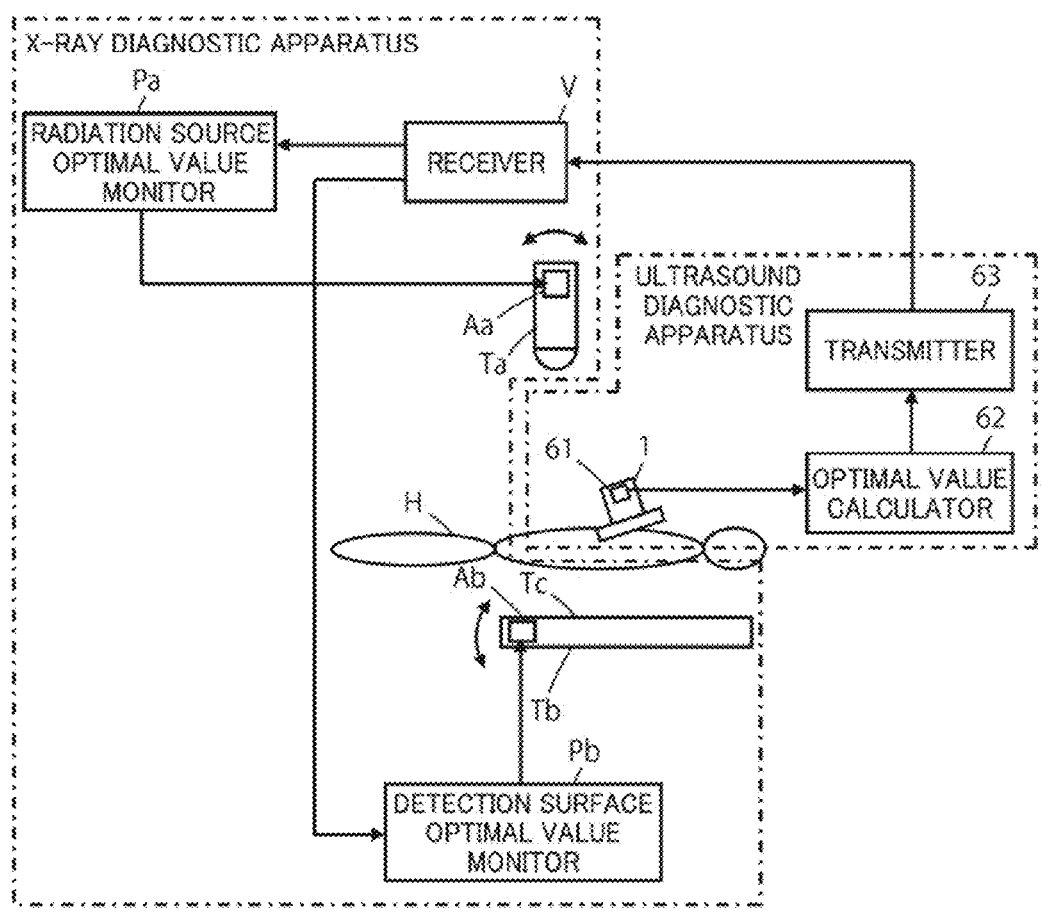
FIG. 12 is a block diagram showing the configuration of an ultrasound diagnostic apparatus according to Embodiment 9 of the invention.

For example, the ultrasound diagnostic apparatus includes, as shown in FIG. 12, an ultrasound probe 1, an ultrasound image generator (not shown), an angle sensor 61 provided in the ultrasound probe 1, an optimal value calculator 62 connected to the angle sensor 61, and a transmitter 63 connected to the optimal value calculator 62. The transmitter 63 is connected to a receiver V of the X-ray diagnostic apparatus.

When combining the ultrasound diagnostic apparatus with the X-ray diagnostic apparatus, the optimal value calculator 62 calculates the radiation source optimal angle of an X-ray source Ta at which the direction of X-ray irradiation from the X-ray source Ta is substantially parallel to the direction of transmission of an ultrasonic beam transmitted from the ultrasound probe 1 and the optimal detection angle of an X-ray image generator Tb at which the normal of a detection surface Tc of the X-ray image generator Tb is substantially parallel to the direction of ultrasonic beam transmission based on angle information obtained from the angle sensor 61. Then, the optimal value calculator 62 transmits the thus calculated radiation source optimal angle and optimal detection angle to the receiver V of the X-ray diagnostic apparatus via the transmitter 63.

In the X-ray diagnostic apparatus, upon receipt of the radiation source optimal angle and the optimal detection angle, the receiver V outputs the radiation source optimal angle to a radiation source optimal value monitor Pa and the optimal detection angle to a detection surface optimal value monitor Pb. The radiation source optimal value monitor Pa displays the radiation source optimal angle inputted from the receiver V and the placement angle of the X-ray source Ta inputted from an angle sensor Aa provided in the X-ray source Ta, and an operator adjusts the placement angle of the X-ray source Ta to the radiation source optimal angle based on this display. In the same manner as above, the detection surface optimal value monitor Pb displays the optimal detection angle inputted from the receptor V and the placement angle of the detection surface Tc of the X-ray image generator Tb inputted from an angle sensor Ab provided in the X-ray image generator Tb, and the placement angle of the detection surface Tc is adjusted to the optimal detection angle based on this display.

According to the embodiment under consideration, an ultrasound image and an X-ray image can be generated so as to accurately correspond to each other in orientation of sections in the subject's body according to the diagnosis.

Embodiment 10

Embodiments 1 to 7 are configured from the complex diagnostic apparatuses each including the ultrasound probe 1, the ultrasound image generator 6, the X-ray source 2 and the X-ray image generator 3 in an integrated form. However, the present invention may also be configured from an X-ray diagnostic apparatus which operates in combination with an ultrasound diagnostic apparatus including an ultrasound probe, an ultrasound image generator and a first angle sensor provided in the ultrasound probe.

In other words, the X-ray diagnostic apparatus according to the embodiment under consideration includes an X-ray source, an X-ray image generator, a second angle sensor provided in the X-ray source, a third angle sensor provided in the X-ray image generator, a receiver connected to the ultrasound diagnostic apparatus to receive angle information from the first angle sensor and an optimal value calculator for calculating, based on the angle information from the first angle sensor received by the receiver, the direction of transmission of an ultrasonic beam transmitted from the ultrasound probe, and the radiation source optimal angle of the X-ray source at which the direction of X-ray irradiation from the X-ray source is substantially parallel to the calculated direction of ultrasonic beam transmission and the optimal detection angle of the X-ray image generator at which the normal of a detection surface of the X-ray image generator is substantially parallel to the calculated direction of ultrasonic beam transmission.

Figure 13:
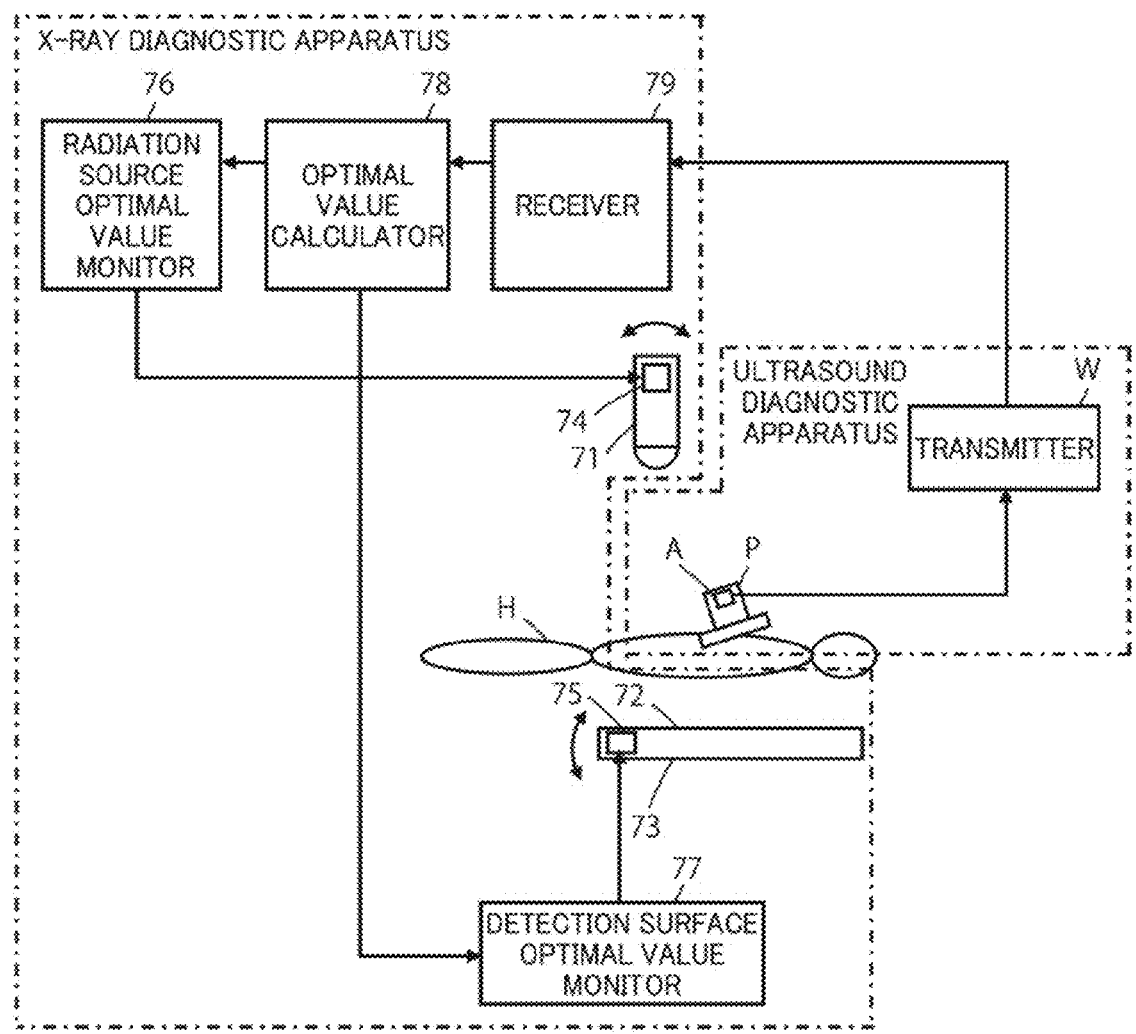
FIG. 13 is a block diagram showing the configuration of an X-ray diagnostic apparatus according to Embodiment 10 of the invention.

For example, as shown in FIG. 13, the X-ray diagnostic apparatus includes an X-ray source 71 and an X-ray image generator 73 having a detection surface 72, and the X-ray source 71 and the X-ray image generator 73 are provided with angle sensors 74 and 75, respectively. The angle sensors 74 and 75 are connected to a radiation source optimal value monitor 76 and a detection surface optimal value monitor 77, respectively. The radiation source optimal value monitor 76 and the detection surface optimal value monitor 77 are connected to a receiver 79 via an optimal value calculator 78.

When combining the X-ray diagnostic apparatus with the ultrasound diagnostic apparatus, angle information of an ultrasound probe P is transmitted from an angle sensor A provided in the ultrasound probe P of the ultrasound diagnostic apparatus to the receiver 79 of the X-ray diagnostic apparatus via a transmitter W. In the X-ray diagnostic apparatus, the angle information received by the receiver 79 is outputted to the optimal value calculator 78. The optimal value calculator 78 calculates, based on angle information from the angle sensor A, the direction of transmission of an ultrasonic beam transmitted from the ultrasound probe P, and the radiation source optimal angle of the X-ray source 71 at which the direction of X-ray irradiation from the X-ray source 71 is substantially parallel to the calculated direction of ultrasonic beam transmission and the optimal detection angle of the X-ray image generator 73 at which the normal of the detection surface 72 of the X-ray image generator 73 is substantially parallel to the calculated direction of ultrasonic beam transmission. The optimal value calculator 78 outputs the calculated radiation source optimal angle to the radiation source optimal value monitor 76 and the calculated optimal detection angle to the detection surface optimal value monitor 77.

The radiation source optimal value monitor 76 displays the radiation source optimal angle inputted from the optimal value calculator 78 and the placement angle of the X-ray source 71 inputted from the angle sensor 74, and an operator adjusts the placement angle of the X-ray source 71 to the radiation source optimal angle based on this display. In the same manner as above, the detection surface optimal value monitor 77 displays the optimal detection angle inputted from the optimal value calculator 78 and the placement angle of the detection surface 72 of the X-ray image generator 73 inputted from the angle sensor 75, and the placement angle of the detection surface 72 is adjusted to the optimal detection angle based on this display.

According to the embodiment under consideration, an ultrasound image and an X-ray image can be generated so as to accurately correspond to each other in orientation of sections in the subject's body according to the diagnosis.

What is claimed is:
1. A complex diagnostic apparatus comprising:
an ultrasound probe configured to transmit and receive an ultrasonic beam toward and from a subject;
an ultrasound image generator configured to generate an ultrasound image based on reception signals outputted from the ultrasound probe;
a radiation source disposed so that its placement angle is variable and configured to emit radiation toward the subject;
a radiographic image generator which is disposed on a side of the subject opposite from the radiation source so that its placement angle is variable, which has a planar detection surface detecting the radiation emitted from the radiation source and which is configured to form a radiographic image according to a dose of a radiation detected on the detection surface;
a first angle sensor provided in the ultrasound probe to detect a placement angle of the ultrasound probe;
a second angle sensor provided in the radiation source to detect a placement angle of the radiation source;
a third angle sensor provided in the radiographic image generator to detect a placement angle of the radiographic image generator; and
an optimal value calculator configured to calculate, based on angle information obtained from the first angle sensor, a direction of transmission of the ultrasonic beam transmitted from the ultrasound probe, and a radiation source optimal angle of the radiation source at which a direction of radiation emitted from the radiation source is substantially parallel to the calculated direction of transmission of the ultrasonic beam and an optimal detection angle of the radiographic image generator at which a normal of the detection surface of the radiographic image generator is substantially parallel to the calculated direction of transmission of the ultrasonic beam, wherein the placement angle of the radiation source is adjusted to the radiation source optimal angle based on angle information obtained from the second angle sensor to emit the radiation and an placement angle of the detection surface of the radiographic image generator is adjusted to the optimal detection angle based on angle information obtained from the third angle sensor to detect the radiation from the radiation source, and wherein the ultrasound image generator generates the ultrasound image in a direction along a scanning surface of the ultrasonic beam, and the radiographic image generator generates the radiographic image in a direction orthogonal to the scanning surface of the ultrasonic beam.

2. The complex diagnostic apparatus according to claim 1, wherein the radiation source emits the radiation to an area restricted to a region of interest on the ultrasound image.

3. The complex diagnostic apparatus according to claim 1, further comprising position sensors provided in the ultrasound probe, the radiation source and the radiographic image generator to detect positions of the ultrasound probe, the radiation source and the radiographic image generator, respectively, wherein the radiation source and the radiographic image generator are disposed so that positional movement is possible, and wherein the optimal value calculator calculates, based on position information obtained from the position sensors, a position of transmission of the ultrasonic beam transmitted from the ultrasound probe, and a radiation source optimal position at which an irradiation axis extending in the direction of radiation emitted from the radiation source and a transmission axis extending in the direction of transmission of the ultrasonic beam overlap each other, and an optimal detection position at which the normal of the detection surface of the radiographic image generator and the transmission axis overlap each other.

4. The complex diagnostic apparatus according to claim 3, further comprising an optimal value monitor configured to display the radiation source optimal position and the optimal detection position.

5. A complex diagnostic apparatus comprising:
an ultrasound probe configured to transmit and receive an ultrasonic beam toward and from a subject;
an ultrasound image generator configured to generate an ultrasound image based on reception signals outputted from the ultrasound probe;
a radiation source disposed so that its placement angle is variable and configured to emit radiation toward the subject;
a radiographic image generator which is disposed on a side of the subject opposite from the radiation source so that its placement angle is variable, which has a planar detection surface detecting the radiation emitted from the radiation source and which is configured to form a radiographic image according to a dose of a radiation detected on the detection surface;
a first angle sensor provided in the ultrasound probe to detect a placement angle of the ultrasound probe;
a second angle sensor provided in the radiation source to detect a placement angle of the radiation source;
a third angle sensor provided in the radiographic image generator to detect a placement angle of the radiographic image generator; and
an optimal value calculator configured to calculate, based on angle information obtained from the first angle sensor, a direction of transmission of the ultrasonic beam transmitted from the ultrasound probe, and a radiation source optimal angle of the radiation source at which a direction of radiation emitted from the radiation source is substantially parallel to the calculated direction of transmission of the ultrasonic beam and an optimal detection angle of the radiographic image generator at which a normal of the detection surface of the radiographic image generator is substantially parallel to the calculated direction of transmission of the ultrasonic beam, wherein the placement angle of the radiation source is adjusted to the radiation source optimal angle based on angle information obtained from the second angle sensor to emit the radiation and an placement angle of the detection surface of the radiographic image generator is adjusted to the optimal detection angle based on angle information obtained from the third angle sensor to detect the radiation from the radiation source, wherein the ultrasound image generator generates the ultrasound image in a direction orthogonal to a scanning surface of the ultrasonic beam, and the radiographic image generator generates the radiographic image in the direction orthogonal to the scanning surface of the ultrasonic beam, and wherein the ultrasound image is generated based on a plurality of ultrasound images obtained by transmission and reception of the ultrasonic beam from and in the ultrasound probe as the scanning surface is successively shifted.

6. The complex diagnostic apparatus according to claim 5, further comprising position sensors provided in the ultrasound probe, the radiation source and the radiographic image generator to detect positions of the ultrasound probe, the radiation source and the radiographic image generator, respectively, wherein the radiation source and the radiographic image generator are disposed so that positional movement is possible, and wherein the optimal value calculator calculates, based on position information obtained from the position sensors, a position of transmission of the ultrasonic beam transmitted from the ultrasound probe, and a radiation source optimal position at which an irradiation axis extending in the direction of radiation emitted from the radiation source and a transmission axis extending in the direction of transmission of the ultrasonic beam overlap each other, and an optimal detection position at which the normal of the detection surface of the radiographic image generator and the transmission axis overlap each other.

7. A complex diagnostic apparatus comprising:
an ultrasound probe configured to transmit and receive an ultrasonic beam toward and from a subject;
an ultrasound image generator configured to generate an ultrasound image based on reception signals outputted from the ultrasound probe;
a radiation source disposed so that its placement angle is variable and configured to emit radiation toward the subject;
a radiographic image generator which is disposed on a side of the subject opposite from the radiation source so that its placement angle is variable, which has a planar detection surface detecting the radiation emitted from the radiation source and which is configured to form a radiographic image according to a dose of a radiation detected on the detection surface;

a first angle sensor provided in the ultrasound probe to detect a placement angle of the ultrasound probe;

a second angle sensor provided in the radiation source to detect a placement angle of the radiation source;

a third angle sensor provided in the radiographic image generator to detect a placement angle of the radiographic image generator; and an optimal value calculator configured to calculate, based on angle information obtained from the first angle sensor, a direction of transmission of the ultrasonic beam transmitted from the ultrasound probe, and a radiation source optimal angle of the radiation source at which a direction of radiation emitted from the radiation source is substantially parallel to the calculated direction of transmission of the ultrasonic beam and an optimal detection angle of the radiographic image generator at which a normal of the detection surface of the radiographic image generator is substantially parallel to the calculated direction of transmission of the ultrasonic beam, wherein the placement angle of the radiation source is adjusted to the radiation source optimal angle based on angle information obtained from the second angle sensor to emit the radiation and an placement angle of the detection surface of the radiographic image generator is adjusted to the optimal detection angle based on angle information obtained from the third angle sensor to detect the radiation from the radiation source, and wherein the complex diagnostic apparatus further comprises at least one of a radiation source drive controller configured to adjust the placement angle of the radiation source based on the radiation source optimal angle and a detection surface drive controller configured to adjust the placement angle of the radiographic image generator based on the optimal detection angle.

8. A complex diagnostic apparatus comprising:

an ultrasound probe configured to transmit and receive an ultrasonic beam toward and from a subject;

an ultrasound image generator configured to generate an ultrasound image based on reception signals outputted from the ultrasound probe;

a radiation source disposed so that its placement angle is variable and configured to emit radiation toward the subject;

a radiographic image generator which is disposed on a side of the subject opposite from the radiation source so that its placement angle is variable, which has a planar detection surface detecting the radiation emitted from the radiation source and which is configured to form a radiographic image according to a dose of a radiation detected on the detection surface;

a first angle sensor provided in the ultrasound probe to detect a placement angle of the ultrasound probe;

a second angle sensor provided in the radiation source to detect a placement angle of the radiation source;

a third angle sensor provided in the radiographic image generator to detect a placement angle of the radiographic image generator; and an optimal value calculator configured to calculate, based on angle information obtained from the first angle sensor, a direction of transmission of the ultrasonic beam transmitted from the ultrasound probe, and a radiation source optimal angle of the radiation source at which a direction of radiation emitted from the radiation source is substantially parallel to the calculated direction of transmission of the ultrasonic beam and an optimal detection angle of the radiographic image generator at which a normal of the detection surface of the radiographic image generator is substantially parallel to the calculated direction of transmission of the ultrasonic beam, wherein the placement angle of the radiation source is adjusted to the radiation source optimal angle based on angle information obtained from the second angle sensor to emit the radiation and an placement angle of the detection surface of the radiographic image generator is adjusted to the optimal detection angle based on angle information obtained from the third angle sensor to detect the radiation from the radiation source, and wherein the complex diagnostic apparatus further comprises an optimal value monitor configured to display the radiation source optimal angle and the optimal detection angle.

9. The complex diagnostic apparatus according to claim 8, further comprising position sensors provided in the ultrasound probe, the radiation source and the radiographic image generator to detect positions of the ultrasound probe, the radiation source and the radiographic image generator, respectively, wherein the radiation source and the radiographic image generator are disposed so that positional movement is possible, and wherein the optimal value calculator calculates, based on position information obtained from the position sensors, a position of transmission of the ultrasonic beam transmitted from the ultrasound probe, and a radiation source optimal position at which an irradiation axis extending in the direction of radiation emitted from the radiation source and a transmission axis extending in the direction of transmission of the ultrasonic beam overlap each other, and an optimal detection position at which the normal of the detection surface of the radiographic image generator and the transmission axis overlap each other.

10. The complex diagnostic apparatus according to claim 9, further comprising an optimal value monitor configured to display the radiation source optimal position and the optimal detection position.

11. A complex diagnostic apparatus comprising:

an ultrasound probe configured to transmit and receive an ultrasonic beam toward and from a subject;

an ultrasound image generator configured to generate an ultrasound image based on reception signals outputted from the ultrasound probe;

a radiation source disposed so that its placement angle is variable and configured to emit radiation toward the subject;

a radiographic image generator which is disposed on a side of the subject opposite from the radiation source so that its placement angle is variable, which has a planar detection surface detecting the radiation emitted from the radiation source and which is configured to form a radiographic image according to a dose of a radiation detected on the detection surface;

a first angle sensor provided in the ultrasound probe to detect a placement angle of the ultrasound probe;

a second angle sensor provided in the radiation source to detect a placement angle of the radiation source;
a third angle sensor provided in the radiographic image generator to detect a placement angle of the radiographic image generator; and
an optimal value calculator configured to calculate, based on angle information obtained from the first angle sensor, a direction of transmission of the ultrasonic beam transmitted from the ultrasound probe, and a radiation source optimal angle of the radiation source at which a direction of radiation emitted from the radiation source is substantially parallel to the calculated direction of transmission of the ultrasonic beam and an optimal detection angle of the radiographic image generator at which a normal of the detection surface of the radiographic image generator is substantially parallel to the calculated direction of transmission of the ultrasonic beam,
wherein the placement angle of the radiation source is adjusted to the radiation source optimal angle based on angle information obtained from the second angle sensor to emit the radiation and an placement angle of the detection surface of the radiographic image generator is adjusted to the optimal detection angle based on angle information obtained from the third angle sensor to detect the radiation from the radiation source, and
wherein the complex diagnostic apparatus further comprises position sensors provided in the ultrasound probe, the radiation source and the radiographic image generator to detect positions of the ultrasound probe, the radiation source and the radiographic image generator, respectively,
wherein the radiation source and the radiographic image generator are disposed so that positional movement is possible, and
wherein the optimal value calculator calculates, based on position information obtained from the position sensors, a position of transmission of the ultrasonic beam transmitted from the ultrasound probe, and a radiation source optimal position at which an irradiation axis extending in the direction of radiation emitted from the radiation source and a transmission axis extending in the direction of transmission of the ultrasonic beam overlap each other, and an optimal detection position at which the normal of the detection surface of the radiographic image generator and the transmission axis overlap each other.

12. The complex diagnostic apparatus according to claim 11, further comprising at least one of a radiation source drive controller configured to adjust a position of the radiation source based on the radiation source optimal position and a detection surface drive controller configured to adjust a position of the radiographic image generator based on the optimal detection position.

13. The complex diagnostic apparatus according to claim 11, further comprising an optimal value monitor configured to display the radiation source optimal position and the optimal detection position.

14. A complex diagnostic apparatus comprising:
an ultrasound probe configured to transmit and receive an ultrasonic beam toward and from a subject;
an ultrasound image generator configured to generate an ultrasound image based on reception signals outputted from the ultrasound probe;
a radiation source disposed so that its placement angle is variable and configured to emit radiation toward the subject;
a radiographic image generator which is disposed on a side of the subject opposite from the radiation source so that its placement angle is variable, which has a planar detection surface detecting the radiation emitted from the radiation source and which is configured to form a radiographic image according to a dose of a radiation detected on the detection surface;
a first angle sensor provided in the ultrasound probe to detect a placement angle of the ultrasound probe;
a second angle sensor provided in the radiation source to detect a placement angle of the radiation source;
a third angle sensor provided in the radiographic image generator to detect a placement angle of the radiographic image generator; and
an optimal value calculator configured to calculate, based on angle information obtained from the first angle sensor, a direction of transmission of the ultrasonic beam transmitted from the ultrasound probe, and a radiation source optimal angle of the radiation source at which a direction of radiation emitted from the radiation source is substantially parallel to the calculated direction of transmission of the ultrasonic beam and an optimal detection angle of the radiographic image generator at which a normal of the detection surface of the radiographic image generator is substantially parallel to the calculated direction of transmission of the ultrasonic beam,
wherein the placement angle of the radiation source is adjusted to the radiation source optimal angle based on angle information obtained from the second angle sensor to emit the radiation and an placement angle of the detection surface of the radiographic image generator is adjusted to the optimal detection angle based on angle information obtained from the third angle sensor to detect the radiation from the radiation source, and
wherein the complex diagnostic apparatus further comprises an image monitor configured to simultaneously display the ultrasound image generated in the ultrasound image generator and the radiographic image generated in the radiographic image generator.

15. The complex diagnostic apparatus according to claim 14, wherein the image monitor displays the ultrasound image and the radiographic image on an identical scale.

16. A method of generating a complex diagnostic image comprising the steps of:
performing transmission and reception of an ultrasonic beam between an ultrasound probe and a subject;
generating an ultrasound image in an ultrasound image generator based on reception signals outputted from the ultrasound probe;
calculating in an optimal value calculator, based on angle information obtained from a first angle sensor provided in the ultrasound probe to detect a placement angle of the ultrasound probe, a direction of transmission of the ultrasonic beam transmitted from the ultrasound probe, and a radiation source optimal angle of a radiation source at which a direction of radiation emitted from the radiation source is substantially parallel to the calculated direction of transmission of the ultrasonic beam and an optimal detection angle of a radiographic image generator at which a normal of a detection surface of the radiographic image generator is substantially parallel to the calculated direction of transmission of the ultrasonic beam;

adjusting an placement angle of the radiation source to the radiation source optimal angle based on angle information obtained from a second angle sensor provided in the radiation source to emit the radiation;

adjusting an placement angle of the detection surface of the radiographic image generator disposed on a side of the subject opposite from the radiation source to the optimal detection angle based on angle information obtained from a third angle sensor provided in the radiographic image generator to detect the radiation from the radiation source; and generating a radiographic image in the radiographic image generator according to a dose of a radiation detected on the detection surface.

17. A complex diagnostic system operating in combination with an ultrasound diagnostic apparatus comprising an ultrasound probe configured to transmit and receive an ultrasonic beam toward and from a subject and an ultrasound image generator configured to generate an ultrasound image based on reception signals outputted from the ultrasound probe; and a radiation diagnostic apparatus comprising a radiation source disposed so that its placement angle is variable and configured to emit radiation toward the subject, and a radiographic image generator which is disposed on a side of the subject opposite from the radiation source so that its placement angle is variable, which has a planar detection surface detecting the radiation emitted from the radiation source and which is configured to generate a radiographic image according to a dose of a radiation detected on the detection surface;

the complex diagnostic system comprising:

a first angle sensor for attaching to the ultrasound probe to detect a placement angle of the ultrasound probe;

a second angle sensor for attaching to the radiation source to detect a placement angle of the radiation source;

a third angle sensor for attaching to the radiographic image generator to detect a placement angle of the radiographic image generator; and an optimal value calculator configured to calculate, based on angle information obtained from the first angle sensor, a direction of transmission of the ultrasonic beam transmitted from the ultrasound probe, and a radiation source optimal angle of the radiation source at which a direction of radiation emitted from the radiation source is substantially parallel to the calculated direction of transmission of the ultrasonic beam and an optimal detection angle of the radiographic image generator at which a normal of the detection surface of the radiographic image generator is substantially parallel to the calculated direction of transmission of the ultrasonic beam, wherein the placement angle of the radiation source is adjusted to the radiation source optimal angle based on angle information obtained from the second angle sensor to emit the radiation and an placement angle of the detection surface of the radiographic image generator is adjusted to the optimal detection angle based on angle information obtained from the third angle sensor to detect the radiation from the radiation source.

18. A ultrasound diagnostic apparatus operating in combination with a radiation diagnostic apparatus comprising a radiation source disposed so that its placement angle is variable and configured to emit radiation toward a subject, a radiographic image generator which is disposed on a side of the subject opposite from the radiation source so that its placement angle is variable, which has a planar detection surface detecting the radiation emitted from the radiation source and which is configured to form a radiographic image according to a dose of a radiation detected on the detection surface, a first angle sensor provided in the radiation source to detect a placement angle of the radiation source, and a second angle sensor provided in the radiographic image generator to detect a placement angle of the radiographic image generator, the ultrasound diagnostic apparatus comprising:

an ultrasound probe configured to transmit and receive an ultrasonic beam toward and from the subject;

an ultrasound image generator configured to generate an ultrasound image based on reception signals outputted from the ultrasound probe;

a third angle sensor provided in the ultrasound probe to detect a placement angle of the ultrasound probe;

an optimal value calculator configured to calculate, based on angle information obtained from the third angle sensor, a direction of transmission of the ultrasonic beam transmitted from the ultrasound probe, and a radiation source optimal angle of the radiation source at which a direction of radiation emitted from the radiation source is substantially parallel to the calculated direction of transmission of the ultrasonic beam and an optimal detection angle of the radiographic image generator at which a normal of the detection surface of the radiographic image generator is substantially parallel to the calculated direction of transmission of the ultrasonic beam; and a transmitter configured to transmit the radiation source optimal angle and the optimal detection angle calculated in the optimal value calculator to the radiation diagnostic apparatus, wherein the placement angle of the radiation source is adjusted to the radiation source optimal angle based on angle information obtained from the first angle sensor to emit the radiation and an placement angle of the detection surface of the radiographic image generator is adjusted to the optimal detection angle based on angle information obtained from the second angle sensor to detect the radiation from the radiation source.

19. A radiation diagnostic apparatus operating in combination with an ultrasound diagnostic apparatus comprising an ultrasound probe configured to transmit and receive an ultrasonic beam toward and from a subject, an ultrasound image generator configured to generate an ultrasound image based on reception signals outputted from the ultrasound probe and a first angle sensor provided in the ultrasound probe to detect a placement angle of the ultrasound probe, the radiation diagnostic apparatus comprising:

a radiation source disposed so that its placement angle is variable and configured to emit radiation toward the subject;

a radiographic image generator which is disposed on a side of the subject opposite from the radiation source so that its placement angle is variable, which has a planar detection surface detecting the radiation emitted from the radiation source and which is configured to generate a radiographic image according to a radiation dose detected on the detection surface;

a second angle sensor provided in the radiation source to detect a placement angle of the radiation source;

a third angle sensor provided in the radiographic image generator to detect a placement angle of the radiographic image generator;

a receiver connected to the ultrasound diagnostic apparatus to receive angle information from the first angle sensor; and an optimal value calculator configured to calculate, based on the angle information from the first angle sensor received by the receiver, a direction of transmission of the ultrasonic beam transmitted from the ultrasound probe, and a radiation source optimal angle of the radiation source at which a direction of radiation emitted from the radiation source is substantially parallel to the calculated direction of transmission of the ultrasonic beam and an optimal detection angle of the radiographic image generator at which a normal of the detection surface of the radiographic image generator is substantially parallel to the calculated direction of transmission of the ultrasonic beam;

wherein the placement angle of the radiation source is adjusted to the radiation source optimal angle based on angle information obtained from the second angle sensor to emit the radiation and an placement angle of the detection surface of the radiographic image generator is adjusted to the optimal detection angle based on angle information obtained from the third angle sensor to detect the radiation from the radiation source.

* * * * *